US009595089B2

(12) United States Patent
Itu et al.

(10) Patent No.: US 9,595,089 B2
(45) Date of Patent: Mar. 14, 2017

(54) METHOD AND SYSTEM FOR NON-INVASIVE COMPUTATION OF HEMODYNAMIC INDICES FOR CORONARY ARTERY STENOSIS

(71) Applicant: SIEMENS HEALTHCARE GMBH, Erlangen (DE)

(72) Inventors: Lucian Mihai Itu, Brasov (RO); Puneet Sharma, Monmouth Junction, NJ (US); Thomas Redel, Poxdorf (DE); Bogdan Georgescu, Plainsboro, NJ (US)

(73) Assignee: SIEMENS HEALTHCARE GMBH, Erlangen (DE)

( * ) Notice: Subject to any disclaimer, the term of this patent is extended or adjusted under 35 U.S.C. 154(b) by 8 days.

(21) Appl. No.: 14/689,083

(22) Filed: Apr. 17, 2015

(65) Prior Publication Data

US 2015/0324962 A1  Nov. 12, 2015

Related U.S. Application Data

(60) Provisional application No. 61/990,775, filed on May 9, 2014.

(51) Int. Cl.
*G06T 7/00* (2006.01)
*G06F 19/00* (2011.01)
(Continued)

(52) U.S. Cl.
CPC ............ *G06T 7/00* (2013.01); *A61B 5/02007* (2013.01); *A61B 5/02028* (2013.01);
(Continued)

(58) Field of Classification Search
CPC ............ G06T 7/00; G06T 2207/10116; G06T 2207/30048; G06T 2207/30104;
(Continued)

(56) References Cited

U.S. PATENT DOCUMENTS 6,236,878 B1  5/2001  Taylor et al.
7,860,290 B2  12/2010  Gulsun et al.
(Continued)

OTHER PUBLICATIONS

Sen et al., "Diagnostic Classification of the Instantaneous Wave-Free Ratio is Equivalent to Fractional Flow Reserve and is Not Improved With Adenosine Administration", Apr. 2013, Journal of the American College of Cardiology, vol. 61, Iss. 13, 1409-1420.*
(Continued)

*Primary Examiner* — Katrina Fujita

(57) ABSTRACT

A method and system for non-invasive hemodynamic assessment of coronary artery stenosis based on medical image data is disclosed. Patient-specific anatomical measurements of the coronary arteries are extracted from medical image data of a patient. Patient-specific boundary conditions of a computational model of coronary circulation representing the coronary arteries are calculated based on the patient-specific anatomical measurements of the coronary arteries. Blood flow and pressure in the coronary arteries are simulated using the computational model of coronary circulation and the patient-specific boundary conditions and coronary autoregulation is modeled during the simulation of blood flow and pressure in the coronary arteries. A wave-free period is identified in a simulated cardiac cycle, and an instantaneous wave-Free Ratio (iFR) value is calculated for a stenosis region based on simulated pressure values in the wave-free period.

37 Claims, 12 Drawing Sheets

(51) Int. Cl.
*A61B 5/02* (2006.01)
*A61B 5/00* (2006.01)

(52) U.S. Cl.
CPC ........ *A61B 5/7278* (2013.01); *G06F 19/3431* (2013.01); *G06F 19/3437* (2013.01); *A61B 2576/00* (2013.01); *A61B 2576/023* (2013.01); *G06T 2207/10116* (2013.01); *G06T 2207/30048* (2013.01); *G06T 2207/30104* (2013.01)

(58) Field of Classification Search
CPC .. G06F 19/12; G06F 19/3431; G06F 19/3437; A61B 5/02007; A61B 5/02028; A61B 5/7278; A61B 2576/00; A61B 2576/023
See application file for complete search history.

(56) References Cited

U.S. PATENT DOCUMENTS

| | | | |
|---|---|---|---|
| 7,953,266 B2 | 5/2011 | Gulsun et al. | |
| 8,098,918 B2 | 1/2012 | Zheng et al. | |
| 8,157,742 B2 | 4/2012 | Taylor | |
| 8,200,466 B2 | 6/2012 | Spilker et al. | |
| 8,249,815 B2 | 8/2012 | Taylor | |
| 8,311,747 B2 | 11/2012 | Taylor | |
| 8,311,748 B2 | 11/2012 | Taylor et al. | |
| 8,311,750 B2 | 11/2012 | Taylor | |
| 8,315,812 B2 | 11/2012 | Taylor | |
| 8,315,813 B2 | 11/2012 | Taylor et al. | |
| 8,315,814 B2 | 11/2012 | Taylor et al. | |
| 8,321,150 B2 | 11/2012 | Taylor | |
| 8,386,188 B2 | 2/2013 | Taylor et al. | |
| 9,247,918 B2 * | 2/2016 | Sharma ................ | A61B 6/507 |
| 9,501,620 B2 * | 11/2016 | Okell ................ | G06F 19/3437 |
| 2010/0017171 A1 | 1/2010 | Spilker et al. | |
| 2010/0067760 A1 | 3/2010 | Zhang et al. | |
| 2011/0224542 A1 | 9/2011 | Mittal et al. | |
| 2012/0022843 A1 | 1/2012 | Ionasec et al. | |
| 2012/0041301 A1 | 2/2012 | Redel | |
| 2012/0041318 A1 | 2/2012 | Taylor | |
| 2012/0041319 A1 | 2/2012 | Taylor et al. | |
| 2012/0041320 A1 | 2/2012 | Taylor | |
| 2012/0041321 A1 | 2/2012 | Taylor et al. | |
| 2012/0041322 A1 | 2/2012 | Taylor et al. | |
| 2012/0041323 A1 | 2/2012 | Taylor et al. | |
| 2012/0041324 A1 | 2/2012 | Taylor et al. | |
| 2012/0041735 A1 | 2/2012 | Taylor | |
| 2012/0041739 A1 | 2/2012 | Taylor | |
| 2012/0053918 A1 | 3/2012 | Taylor | |
| 2012/0053919 A1 | 3/2012 | Taylor | |
| 2012/0053921 A1 | 3/2012 | Taylor | |
| 2012/0059246 A1 | 3/2012 | Taylor | |
| 2012/0072190 A1 | 3/2012 | Sharma et al. | |
| 2012/0121151 A1 | 5/2012 | Bernhardt et al. | |
| 2012/0150516 A1 | 6/2012 | Taylor et al. | |
| 2012/0203530 A1 | 8/2012 | Sharma et al. | |
| 2012/0243761 A1 | 9/2012 | Senzig et al. | |
| 2013/0054214 A1 | 2/2013 | Taylor | |
| 2013/0064438 A1 | 3/2013 | Taylor et al. | |
| 2013/0132054 A1 | 5/2013 | Sharma et al. | |
| 2013/0246034 A1 | 9/2013 | Sharma et al. | |
| 2014/0058715 A1 | 2/2014 | Sharma et al. | |
| 2014/0180140 A1 * | 6/2014 | Alpert ................ | A61B 5/0004 600/486 |
| 2015/0112182 A1 | 4/2015 | Sharma et al. | |
| 2015/0374243 A1 * | 12/2015 | Itu ................ | G06F 19/3437 703/2 |

OTHER PUBLICATIONS

C.A. Taylor, et al., "Open Problems in Computational Vascular Biomechanics: Hemodynamics and Arterial Wall Mechanics," Comput Methods Appl Mech. Eng., vol. 198, pp. 3514-3523, 2009.

Chamuleau et al, "Association between coronary lesion severity and distal microvascular resistance in patients with coronary artery disease," Am J Physiol Heart Circ Physiol, vol. 285, pp. H2194-H2200, 2003.

De Bruyne et al., "Simultaneous Coronary Pressure and Flow Velocity Measurements in Humans," Circulation, vol. 94, pp. 1842-1849, 1996.

H. Vernon Anderson et al., "Coronary Atery Flow Velocity is Related to Lumen Area and Regional Left Ventricular Mass," Circulation, vol. 102, pp. 48-54, 2000.

Annemiek J. M. Cornelissen et al: "Balance between myogenic, flow-dependent, and metabolic flow control in coronary arterial tree: a model study", AJP: Heart and Circulatory Physiology, vol. 282, No. 6, Jun. 1, 2002 (Jun. 1, 2002), pp. H2224-H2237, XP055213954, ISSN: 0363-6135, DOI: 10.1152/ajpheart.00491. 2001.

A.R. Pries et al: "Remodeling of Blood Vessels: Responses of Diameter and Wall Thickness to Hemodynamic and Metabolie Stimuli", EPO Form 1703 01.91TAI Hypertension, vol. 46, No. 4, Sep. 19, 2005 (Sep. 19, 2005), pp. 725-731, XP055127457, ISSN: 0194-911X, DOI:10.1161/01.HYP.0000184428.16429.be.

E. Shalman et al: Numerical modeling of the flow in stenosed coronary artery. The relationship between main hemodynamic parameters II , Computers in Biology and Medicine, vol. 1. 32, No. 5, Sep. 1, 2002 (Sep. 1, 2002), pp. 329-344, XP055198775 / Sep. 1, 2002.

Kagiyama Mitsuyasu et al: "Model analysis of coronary hemodynamics incorporating autoregulation", Systems and Computers in Japan, vol. 35, No. 14, Dec. 1, 2004 (Dec. 1, 2004), pp. 21-31, XP055213930, ISSN: 0882-1666, 001: 10.10021scj.10709.

Colin Berry et al: "VERIFY (VERification of Instantaneous Wave-Free Ratio and Fractional Flow Reserve for the Assessment of Coronary Artery Stenosis Severity in Everyday Practice)", Journal of the American College of Caroiology, vol. 61, No. 13, Apr. 1, 2013 (Apr. 1, 2013), pp. 1421-1427, XP055214390, ISSN: 0735-1097, 001: 10.1016/j.jacc2012.09.065.

* cited by examiner

METHOD AND SYSTEM FOR NON-INVASIVE COMPUTATION OF HEMODYNAMIC INDICES FOR CORONARY ARTERY STENOSIS

This application claims the benefit of U.S. Provisional Application No. 61/990,775, filed May 9, 2014, the disclosure of which is herein incorporated by reference.

BACKGROUND OF THE INVENTION

The present invention relates to non-invasive functional assessment of coronary artery stenosis, and more particularly, to non-invasive functional assessment of coronary artery stenosis from medical image data and blood flow simulations.

Cardiovascular disease (CVD) is the leading cause of deaths worldwide. Among various CVDs, coronary artery disease (CAD) accounts for nearly fifty percent of those deaths. Despite significant improvements in medical imaging and other diagnostic modalities, the increase in premature morbidity and mortality for CAD patients is still very high. The current clinical practice for diagnosis and management of coronary stenosis involves the assessment of the diseased vessel either visually or by Quantitative Coronary Angiography (QCA). Such assessment provides the clinician with an anatomical overview of the stenosis segment and parent vessel, including the area reduction, lesion length, and minimal lumen diameter, but does not provide a functional assessment of the effect of the lesion on blood flow through the vessel.

The instantaneous wave-Free Ratio (iFR) has been proposed as an index for classifying coronary artery stenoses into hemodynamically significant and non-significant lesions. Measuring iFR typically requires invasive pressure measurements performed both proximal and distal to a stenosis acquired at a rest state of the patient by inserting a coronary pressure wire into the stenosed vessel. The iFR is then calculated as the average pressure distal to a stenosis during the diastolic wave-free period divided by the average aortic pressure during the wave-free period. However, invasive pressure measurements acquired using a pressure involve risks associated with the intervention necessary to insert the pressure wire into the stenosed vessel, and, for a very narrow stenosis, the pressure wire may induce an additional pressure drop.

BRIEF SUMMARY OF THE INVENTION

The present invention provides a method and system for non-invasive computation of hemodynamic indices for a coronary artery stenosis. Embodiments of the present invention provide a method for non-invasive computation of a pressure difference over a coronary artery stenosis and hemodynamic indices derived from the pressure difference from medical images of vessels acquired when a patient is in a rest-state. Embodiments of the present invention compute the instantaneous wave-free ratio (iFR) for a stenosis from medical images without requiring the need for inserting a pressure wire across the stenosis. The iFR and other hemodynamic metrics can be used for functional assessment of the coronary artery stenosis.

In one embodiment of the present invention, patient-specific anatomical measurements of the coronary arteries are extracted from medical image data of a patient. Patient-specific boundary conditions of a computational model of coronary circulation representing the coronary arteries are calculated based on the patient-specific anatomical measurements of the coronary arteries. Blood flow and pressure in the coronary arteries are simulated using the computational model of coronary circulation and the patient-specific boundary conditions and coronary autoregulation is modeled during the simulation of blood flow and pressure in the coronary arteries. A hemodynamic index is calculated for at least one stenosis region in the coronary arteries based on the simulated blood flow and pressure. A wave-free period can be identified in at least one simulated cardiac cycle in the simulation of blood flow and pressure in the coronary arteries, and the hemodynamic index calculated for the at least one stenosis region can be an instantaneous wave-Free Ratio (iFR) value calculated based on simulated pressure values in the wave-free period identified in the at least one simulated cardiac cycle.

These and other advantages of the invention will be apparent to those of ordinary skill in the art by reference to the following detailed description and the accompanying drawings.

DETAILED DESCRIPTION

The present invention relates to a method and system for non-invasive computation of hemodynamic indices for coronary artery stenosis using medical image data and blood flow simulations. Embodiments of the present invention are described herein to give a visual understanding of the methods for simulating blood flow and assessing coronary artery stenosis. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
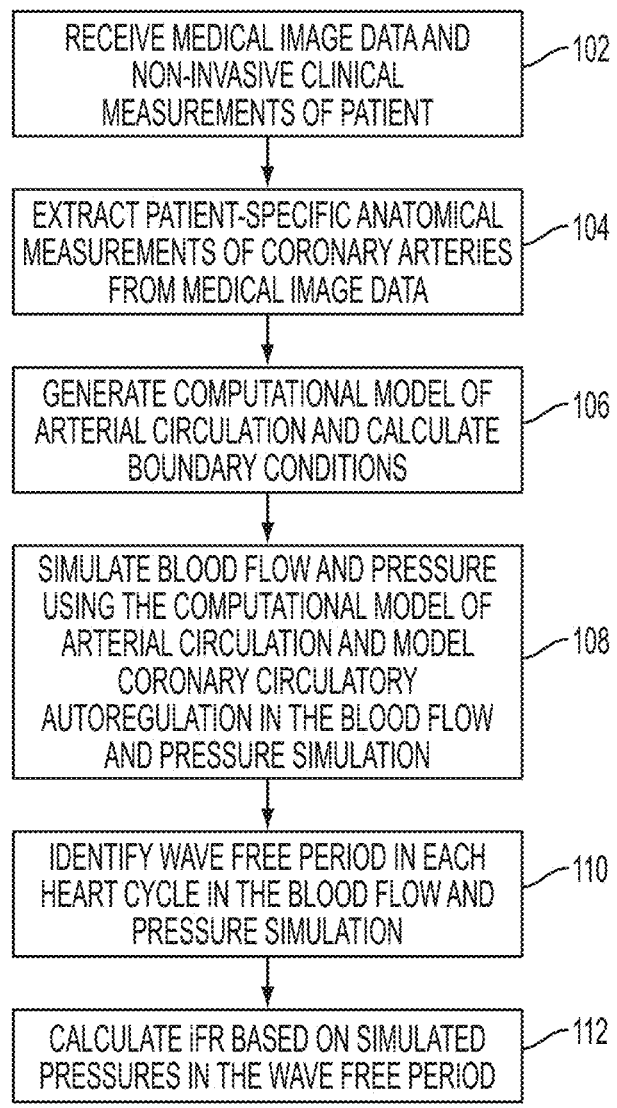
FIG. 1 illustrates a method for non-invasive computation of a hemodynamic index for a coronary artery stenosis according to an embodiment of the present invention.

FIG. 1 illustrates a method for non-invasive computation of a hemodynamic index for a coronary artery stenosis according to an embodiment of the present invention. The method of FIG. 1 transforms medical image data of a patient to extract the patient-specific geometry of the coronary arteries, generate a model of coronary arterial circulation, simulate patient-specific blood flow and pressure in the coronary arteries, and calculate one or more hemodynamic indices for a coronary artery stenosis without the use of invasive pressure measurements acquired via a pressure wire across the stenosis. As described herein, the method of FIG. 1 computes the instantaneous wave-free ratio (iFR) for a coronary artery stenosis without using invasive pressure measurements. However, the present invention is not limited to iFR and the method of FIG. 1 may be similarly applied to compute other hemodynamic indices as well.

Referring to FIG. 1, at step 102, medical image data and non-invasive clinical measurements of a patient are received. Medical image data from one or multiple imaging modalities can be received. For example, the medical image data can include, computed tomography (CT), Dyna CT, magnetic resonance (MR), Angiography, Ultrasound, Single Photon Emission computed Tomography (SPECT), and any other type of medical imaging modality. The medical image data can be 2D, 3D, or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient.

In an advantageous embodiment, 3D coronary CT angiography (CTA) images are acquired on a CT scanner. The CTA images ensure that the coronary vasculature, including the vessel(s) that contain the stenosis, is adequately imaged using a contrast agent that is injected into the patient. At this stage, the clinician may be provided with an option of identifying lesions (stenoses) of interest by interactively viewing them on the images. This step can also be performed on a patient-specific anatomical model that is extracted from the image data (step 104). Alternatively, the stenoses may be automatically detected in the image data using an algorithm for automatic detection of coronary artery stenosis, such as the method for automatic detection of coronary artery stenosis described in United States Published Patent Application No. 2011/0224542, which is incorporated herein by reference. In addition to the medical image data, other non-invasive clinical measurements, such as the patient's heart rate and systolic and diastolic blood pressure are also acquired.

At step 104, patient-specific anatomical measurements of the coronary arteries are extracted from the medical image data. In an advantageous embodiment, the medical image data is acquired at rest-state and the measurements of the coronary arteries are extracted from the medical image data acquired at rest-state. The measurements of the coronary arteries can be extracted by generating a patient-specific anatomical model of the coronary artery tree from the medical image data. The patient-specific anatomical model may be a patient-specific anatomical model of any portion of the full coronary artery tree of the patient. In order to generate the patient-specific anatomical model of the coronary artery tree, the coronary arteries can be segmented in the 3D medical image data using an automated coronary artery centerline extraction algorithm. For example, the coronary arteries can be segmented in a CT volume using the method described United States Published Patent Application No. 2010/0067760, which is incorporated herein by reference. Once a coronary artery centerline tree is extracted, cross-section contours can be generated at each point of the centerline tree. The cross-section contour at each centerline point gives a corresponding cross-section area measurement at that point in the coronary artery. A geometric surface model is then generated for the segmented coronary arteries. For example, methods for anatomical modeling of the coronary arteries are described in U.S. Pat. No. 7,860,290 and U.S. Pat. No. 7,953,266, both of which are incorporated herein by reference. In addition to the coronaries, the patient-specific anatomical model can include the aortic root together with the proximal part of the aorta. A detailed 3D model of each stenosis can also be extracted using similar algorithms, which includes the quantification of the proximal vessel diameter and area, distal vessel diameter and area, minimal lumen diameter and area, and length of stenosis.

The above described anatomical modeling tasks can be performed automatically or can be user-driven, thereby allowing the user (clinician) to interactively make changes to the anatomical models to analyze the effects of such changes on the subsequent computation of FFR. In addition to the coronary vessel tree, the myocardium may also be segmented (either automatically or manually) in the medical image data to determine an estimate of the left ventricular mass, which in a possible implementation, may be used to estimate the absolute resting flow for the patient which is used to calculate boundary conditions for a computational blood flow and pressure simulation. Alternatively, the resting flow could also be computed based on the total volume of the segmented coronary tree, or from the outlet radius of the different coronary vessels. In an exemplary embodiment, a patient-specific anatomical model of the heart that is automatically generated from the image data may be used for this purpose. The anatomical heart model is a multi-component model having multiple cardiac components, including the four chambers (left ventricle, left atrium, right ventricle, and right atrium). The anatomical heart model may also include components such as the heart valves (aortic valve, mitral valve, tricuspid valve, and pulmonary valve) and the aorta. Such a comprehensive model of the heart is used to capture a large variety of morphological, functional, and pathological variations. A modular and hierarchical approach can be used to reduce anatomical complexity and facilitate an effective and flexible estimation of individual anatomies. The 4D anatomical heart model can be generated by generating individual models of each heart component, for example using marginal space learning (MSL), and then integrating the heart component models by establishing mesh point correspondence. Additional details regarding generation of such a 4D patient-specific heart model are described in United States Published Patent Application No. 2012/0022843, which is incorporated herein by reference.

At step 106, a computational model of coronary arterial circulation is generated based on the patient-specific anatomical measurements of the coronary arteries, and inlet and outlet boundary conditions are calculated. In the method of FIG. 1, the iFR value for a stenosis is based on pressure vales computed by simulating blood flow and pressure through the coronary artery tree for a patient at a rest state. For an efficient clinical workflow for evaluating iFR via blood flow and pressure simulations, a balance between model complexity and computation time, without compromising the accuracy of the results, is desirable. In an advantageous embodiment of the present invention, reduced-order models can be used for the patient-specific blood flow simulation, which enables the assessment of the functional significance of a coronary artery stenosis. The reduced-order models provide accurate estimates of flow and pressure distribution in the vessel tree, and are computationally efficient, thus enabling a seamless integration with the clinical workflow. Although a reduced order model of coronary arterial circulation is described herein, the present invention is not limited thereto, and a full-scale model or a multi-scale model can be used as well.

Figure 2:
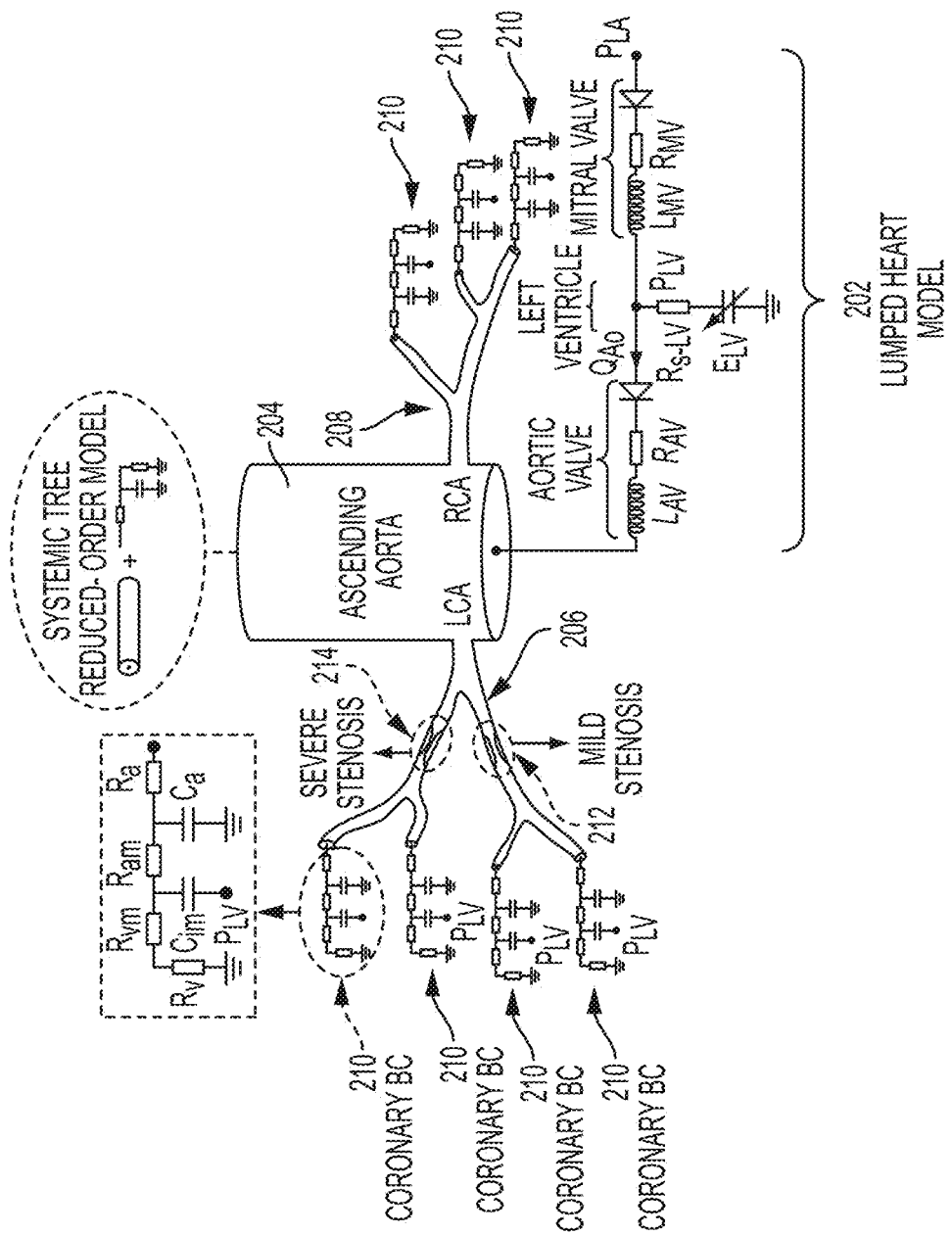
FIG. 2 illustrates a computational model of coronary arterial circulation according to an embodiment of the present invention.

FIG. 2 illustrates a computational model of coronary arterial circulation according to an embodiment of the present invention. As shown in FIG. 2, a heart model 202 is coupled at the root of the aorta. The heart model 202 may be implemented as a lumped model parameterized through patient-specific data as shown in FIG. 2, or may be implemented as a full 3D heart model. Large arteries, such as the aorta 204 together with the large arteries supplied by the aorta (e.g., subclavian, brachiocephalic, common carotid, etc.), the left coronary artery (LCA) 206, and the right coronary artery 208 can be represented as 1D blood flow models or full 3D models. Furthermore, semi-analytical circulatory models can be used either separately for certain arterial segments, or embedded within the 1D or 3D models. The vessel walls can be modeled as a purely elastic or visco-elastic material. The wall properties may be determined through an empirical relationship fit to measured data or based on patient-specific estimations of wall compliance. In the model of coronary arterial circulation of FIG. 2, all microvascular beds are simulated through lumped parameter models 210 which account for the resistance applied to the blood flow and for the compliance of the distal vessels. The coronary vascular bed is modeled through such lumped parameter models 210, which are adapted to the coronary circulation in the sense that they take into account the effects of the myocardial contraction on the flow waveform. Stenosis segments 212 and 214 (i.e., regions in the vessels where a stenosis or a narrowing is detected) are shown in the model of coronary arterial circulation. The stenosis segments 212 and 214 cannot be simulated using the 1D blood flow models since there is a high variation in cross-sectional area and the shape of the stenosis influences the blood flow behavior and especially the trans-stenotic pressure drop which plays a major role in the assessment of the functional importance of such a stenosis. Accordingly, when 1D blood flow models are used for the coronary arteries, a full 3D model or a reduced-order stenosis pressure drop model can be used for each stenosis segment 212 and 214.

The inlet boundary condition for the coronary artery blood flow can be prescribed through an implicit coupling with the heart model 202, or through measured pressure or flow data (e.g., acquired through various imaging techniques). The coronary arteries 206 and 208 can be modeled as axi-symmetric 1-D vessel segments, where the blood-flow satisfies the following properties: conservation of mass, conservation of momentum, and a state equation for wall deformation:

$$\frac{\partial A(t)}{\partial t} + \frac{\partial q(t)}{\partial x} = 0 \quad (1)$$

$$\frac{\partial q(t)}{\partial t} + \frac{\partial}{\partial t}\left(\alpha \frac{q^2(t)}{A(t)}\right) + \frac{A(t)}{\rho}\frac{\partial p(t)}{\partial x} = K_R \frac{q(t)}{A(t)} \quad (2)$$

-continued $$p(t) = \frac{4}{3}\frac{Eh}{r_0}\left(1 - \sqrt{\frac{A_0}{A(t)}}\right), \quad (3)$$

where q is the flow rate, A is the cross-sectional area, p is the pressure, $\alpha$ is the momentum-flux correction coefficient, $K_R$ is a friction parameters, $\rho$ is the density, E is the Young modulus, h is the wall thickness and $r_0$ is the initial radius. The wall properties may be determined through an empirical relationship fit to the measured data in the extracted patient-specific anatomical model or based on patient-specific estimations of the wall compliance. Other alternative formulations of the quasi-1-D flow equations can also be used, modeling the effects of visco-elasticity, non-Newtonian behavior, etc.

At each junction (bifurcations, anastomoses) of the circulation model, continuity of total pressure and flow should be maintained. Additionally, loss coefficients may be introduced which account for the energy loss at the junctions. These loss coefficients may depend on the angles between the vessel segments or may be derived from experimental data. The above quasi 1-D equations (Equations 1-3) are derived by considering a series of simplifying assumptions which all hold well for normal, healthy vessels. One of the assumptions is that the axial velocity is dominant and the radial components are negligible. This assumption no longer holds in case of sudden changes in lumen diameter, e.g. for a stenosis, and the radial components can no longer be excluded. Hence, the quasi 1-D equations do not correctly capture the pressure drop across the stenosis. In a possible implementation, full scale 3D models can be used for blood flow and pressure simulation in stenosis regions 212 and 214. In this case, the patient-specific 3D geometric model of the stenosis extracted from the medical image data (e.g., CTA data) is used in conjunction with quantitative coronary angiography (QCA)-like measures to personalize the stenosis model for the individual patient. In an alternative implementation, semi-empirical stenosis models can be included in the 1-D blood flow models, which produce accurate results as compared to full scale models. For example, in the model below, the pressure drop is expressed as a sum of three terms (viscous term, turbulent or Bernoulli term, and inertance term):

$$\Delta P_s = \frac{\mu K_v}{2\pi r_0^3}q + \frac{\rho K_t}{2A_0^2}\left(\frac{A_0}{A_s} - 1\right)^2|q|q + \frac{\rho K_u L_s}{A_0}\frac{\partial q}{\partial t}, \quad (4)$$

where $\mu$ is the blood viscosity, $L_s$ is the stenosis length, $K_v$, $K_t$ and $K_u$ are the viscous, turbulent, and inertance coefficients, respectively (all the quantities indexed with 0 refer to the normal dimensions while the quantities indexed with s refer to the stenosed values). In an advantageous embodiment, such a semi-empirical model for each stenosis segment (212 and 214) is coupled with the vessel tree (and the underlying heart and coronary bed models) to compute the physiological pressure drop across the stenosis. It is to be understood that the present invention is not limited to the semi-empirical stenosis model of Equation (4), and other such models of the stenosis, with multiple pressure drop factors, may be used alternatively. Regarding coupling of the reduced-order or full-order stenosis model to the rest of the coronary vessel tree, in a first possible implementation, the momentum equation is adapted and the additional pressure drop determined by the turbulent term is included on the right hand side of the equation as an additional loss term. In a second possible implementation, the regular momentum equation is disregarded completely and replaced by Equation (2). The segments treated as stenosis segments are coupled to the regular segments of the coronary vessel tree by considering continuity of total pressure and flow rate.

An important aspect of the flow simulations is represented by the outlet boundary conditions at the termination of the coronary vessel tree (outflow boundary conditions). Generally, pressure, flow, or a relationship between flow and pressure may be imposed at the terminal sites of the arterial vessel tree. If measured data, e.g. time-varying velocity, flow rate, or even pressure, are available, they can be readily applied. In the absence of such information (which is typically the case), embodiments of the present invention calculate special boundary conditions that model the behavior of the distal arterial segments. For example, lumped parameters models (as in FIG. 2) or microvascular wave propagation models can be used to determine the outlet boundary conditions. In an advantageous implementation, as shown in FIG. 2, the microvascular beds are modeled through lumped or 0-D models 210. In this case, the systemic beds can be represented by regular windkessel elements containing varying number of elements (for example, between two and four elements), while coronary beds are represented by special models which account for the influence of the myocardial contraction on the flow waveform (low during systole and high during early diastole). FIG. 2 displays an example of such specialized models for the coronary circulation and presents the detailed elements of this type of boundary condition. In the lumped parameter models 210 of FIG. 2, $R_a$ denotes proximal arterial resistance, $C_a$ denotes arterial compliance, $R_{am}$ denotes microvascular arterial resistance, $C_{im}$ denotes intra-myocardial compliance, $R_{vm}$ denotes microvascular venous resistance, and $R_v$ denotes venous resistance.

The main characteristic of such lumped models is that the myocardial contraction is taken into account by introducing the left or right ventricular pressure, depending on the location of the coronary tree on the heart. The model displayed in FIG. 4 treats the microvascular bed as a single unit, but it is also possible to utilize more specialized models which consider separately the contribution of the subepicardial and subendocardial microvascular beds. Generally, subepicardial vessels are less affected by heart contraction (they represent the outer layers of the myocardium), while subendocardial vessels are more affected by the action of the contraction (they represent the inner layers, closer to the heart chambers). This is the main reason why subendocardial are more prone to ischemia and to myocardial infarction.

Since the resistance values of the large vessels are very small compared to the resistances of the arterioles and capillaries, the overall pressure levels are almost solely determined by the microvascular beds. The resistance values inside the systemic or coronary lumped models for the rest state may be obtained from patient-specific measurements, from literature data, or from the non-linear relationship between resistances and lumen size. Compliances play a secondary role since they only influence the transient values and not the average pressures which are of interest for the evaluation of iFR. Coronary auto-regulation protects the myocardium against ischemia during rest state and leads to decreased resistances for the diseased vessel, the reference value being the flow which has to be identical to the non-diseased case. The rest state outlet boundary conditions can thus be modeled using this information.

In an exemplary embodiment, the parameters that are estimated to determine the rest state outlet boundary conditions are the mean arterial pressure (MAP) and the coronary microvascular resistances (the resistances of the proximal epicardial arteries are negligible compared to the microvascular resistances). Since iFR uses only average measures of pressures (distal and proximal to the stenosis) in the wave free period of diastole, compliances need not be estimated accurately because they only influence the waveform of pressure and flow, but not the average values, which are only determined by the resistances. MAP can be easily measured non-invasively based on the patient's heart rate, systolic blood pressure, and diastolic blood pressure. In particular, the MAP can be calculated as:

$$MAP = DBP + \left[\frac{1}{3} + (HR \cdot 0.0012)\right] \cdot (SBP - DBP), \quad (5)$$

where HR, SBP, and DBP denote the patient's heart rate, systolic blood pressure, diastolic blood pressure, respectively, which are measured non-invasively.

The rest-state cardiac microvascular resistances can be calculated as follows. The total myocardial perfusion $q_{rest}$ can be estimated using the rate-pressure product (RPP) relationship. The RPP is the product of the heart rate and the systolic blood pressure. Starting from the RPP, the resting perfusion $q_{rest}$ can be estimated as:

$$q_{rest} = 8 \cdot \{[0.7 \cdot (HR \cdot SBP) \cdot 10^{-3}] - 0.4\} [\text{ml/min}/100 \text{ g}], \quad (6)$$

where HR is the heart rate and SBP is the systolic blood pressure. It can be noted that this relationship is only valid if the flow meets the oxygen demand of the subject. The total resting coronary flow can then be estimated based on the resting perfusion $q_{rest}$ and the mass of the patient's left ventricle (LV). The mass of the left ventricle can be estimated based on quantities derived from segmentation of the medical image data. In one possible implementation, the myocardium is segmented using automatic heart chamber segmentation, for example using a MSL machine-learning based method. The volume can be automatically calculated from the segmented myocardium, for example using the method described in U.S. Pat. No. 8,098,918, entitled "Method and System for Measuring Left Ventricle Volume", which is incorporated herein by reference. The LV volume is then multiplied by the density to provide the mass of the LV ($M_{LV}$). Other possible methods for calculating the mass of the LV can be used as well.

Next, in order to determine the absolute value of the resting flow, the resting perfusion can be multiplied by the myocardial mass. In normal hearts, it is generally assumed that the left ventricle represents two thirds of the total mass, while the right ventricle and atria represent the other third. Accordingly, once the left ventricular mass $M_{LV}$ is determined, the absolute resting flow can be determined as:

$$Q_{rest} = q_{rest} \cdot 1.5 \cdot M_{LV} [\text{ml/min}]. \quad (7)$$

Having determined that the flow rate is proportional to the cube of the radius, absolute resting flow, which is the sum of all outflow flows of the coronary vessels may be expressed as:

$$Q_{rest} = \sum_{i=1}^{n} k \cdot r_i^3 = \sum_{i=1}^{n} Q_i. \tag{8}$$

The terminal resistance for each vessel branch is then calculated. In particular, the terminal resistance can be calculated using the following relationship:

$$R_i = \frac{MAP}{Q_i}. \tag{9}$$

$Q_i$ is determined by:

$$\frac{Q_i}{Q_{rest}} = \frac{k \cdot r_i^3}{\sum_{j=1}^{n} k \cdot r_j^3} = \frac{r_i^3}{\sum_{j=1}^{n} r_j^3}, \tag{10}$$

and hence:

$$Q_i = \frac{Q_{rest} \cdot r_i^3}{\sum_{j=1}^{n} r_j^3}, \tag{11}$$

where $r_i$ is the terminal radius of a vessel branch (equal to half of the terminal diameter $d_i$) and n is a power coefficient. Thus, the terminal resistance at each vessel can be calculated as:

$$R_i = \frac{MAP}{Q_i} = \frac{MAP \cdot \sum_{j=1}^{n} r_j^3}{Q_{rest} \cdot r_i^3}. \tag{12}$$

Returning to FIG. 1, at step 108, blood flow and pressure are simulated using the computational model of coronary arterial circulation and coronary circulatory autoregulation is modeled in the blood flow and pressure simulation. The simulation incrementally computes blood flow rates and pressure values within the coronary arteries over a period of time at each of a plurality of time steps using the computational model of coronary arterial circulation. The simulation can be run over a plurality of heart cycles, each corresponding to a heartbeat. The flow and pressure computations may be performed using Computational Fluid Dynamics (CFD), or any other standard numerical techniques, such as but not limited to, finite-element method, finite-difference method, finite-volume method, boundary element method, embedded boundary method, immersed boundary method, lattice Boltzmann method, etc.

Figure 3:
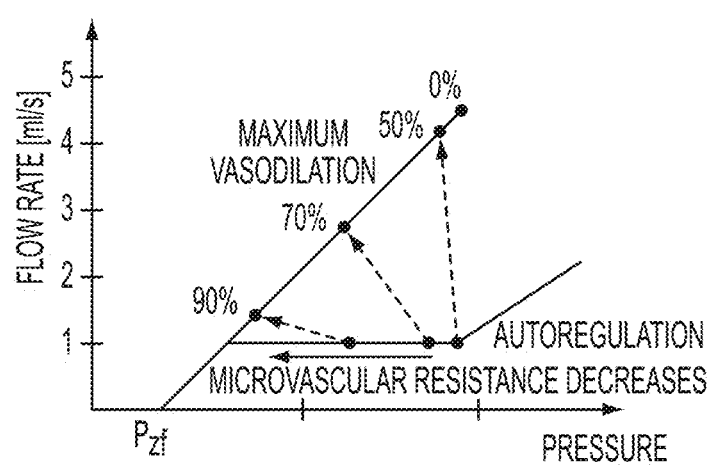
FIG. 3 illustrates coronary circulatory autoregulation.

According to an advantageous embodiment of the present invention, coronary circulatory autoregulation is modeled in the blood flow and pressure simulation. Coronary autoregulation plays an important role in coronary hemodynamics. The purpose of coronary autoregulation is to maintain a certain level of myocardial perfusion, given by the myocardial oxygen demand, to the microvascular beds perfused by arteries which may or may not contain stenoses. FIG. 3 illustrates coronary circulatory autoregulation. As shown in FIG. 3, the autoregulatory mechanism adapts the microvascular resistances so as to maintain perfusion at the level dictated by the myocardial oxygen demand. Since microvascular resistance has a certain minimum threshold value, when a stenosis is very severe and the pressure distal to the stenosis decreases considerably, autoregulation reaches its limit and the myocardial perfusion decreases below the required level, leading to myocardial ischemia.

In order to accurately determine iFR for a stenosis non-invasively based on blood flow and pressure simulations without explicitly measuring the pressure difference across the stenosis, coronary autoregulation has to be taken into consideration. According to an advantageous embodiment, in order to model coronary autoregulation, the microvascular resistances at each outlet of the coronary arterial circulation model (e.g., FIG. 2) are calculated as described above. Next, an equivalent coronary microvascular resistance is calculated for each coronary artery based on the microvascular resistances calculated at the outlets of the coronary artery. The equivalent coronary microvascular resistance of each vessel (branch) i in the coronary tree, $(R_{t-microv})_i$, can be calculated as:

$$(R_{t-microv})_i = \frac{1}{\sum_j 1/(R_{t-microv})_j} \tag{13}$$

where $(R_{t-microv})_j$ is the total microvascular resistance for each terminal branch j. Once the equivalent microvasculature resistance is calculated for each branch in the coronary artery tree, the blood flow and pressure simulation can be performed and an algorithm (Algorithm 1 of FIG. 4) for modeling coronary autoregulation can be applied for each coronary tree during the simulation in order to adjust the microvascular resistances to model the effect of coronary autoregulation.

Figure 4:
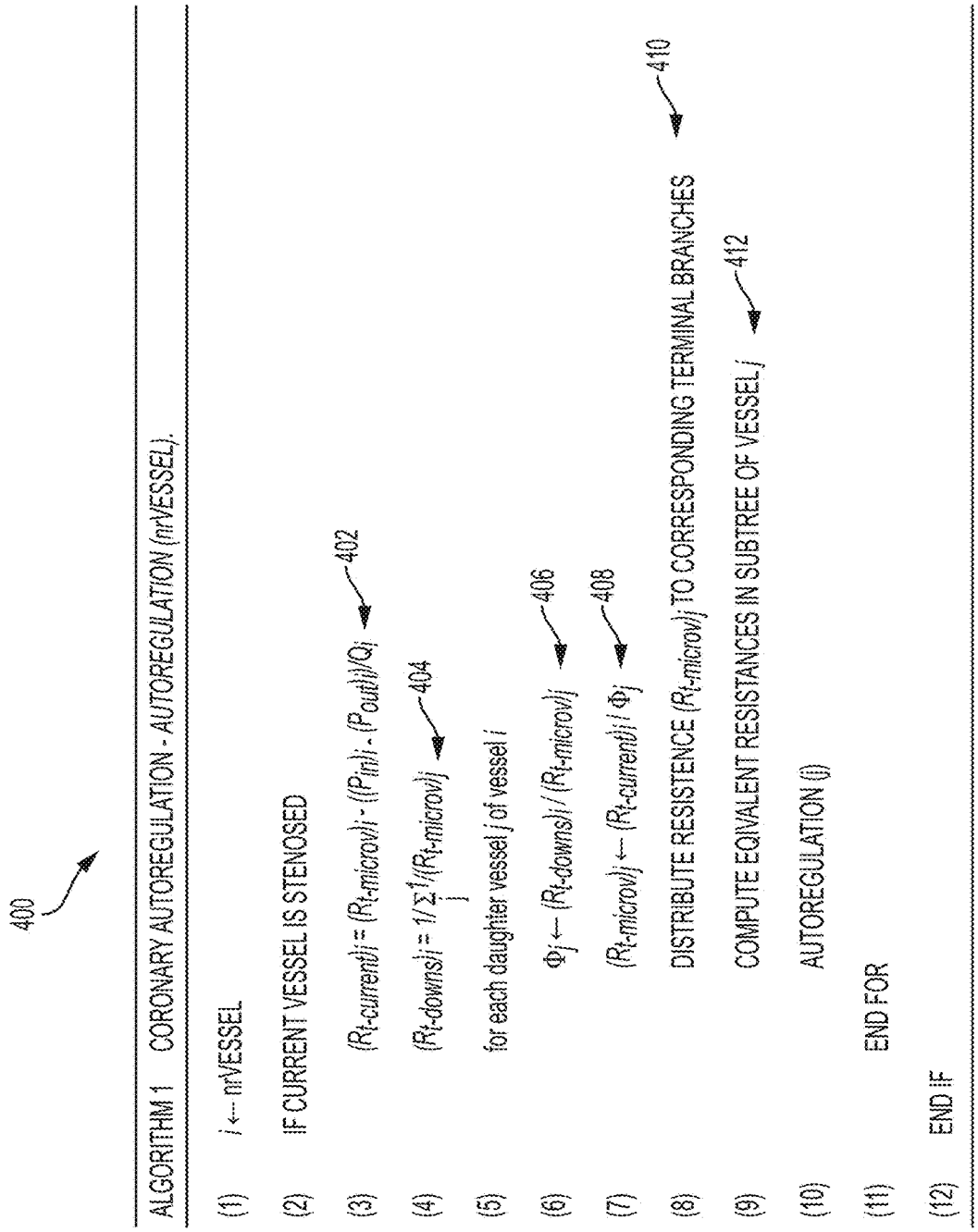
FIG. 4 illustrates an algorithm for modeling coronary circulatory autoregulation in a computational blood flow simulation according to an embodiment of the present invention.

FIG. 4 illustrates an algorithm for modeling coronary autoregulation in a simulation of blood flow and pressure in the coronary arteries according to an embodiment of the present invention. In an advantageous implementation, the algorithm 400 of FIG. 4 (Algorithm 1) can be performed at the end of each cardiac cycle in the blood flow and pressure simulation for each coronary artery tree. The algorithm 400 has an input parameter of nrVessel, which is a number identifying a current vessel or branch in the coronary artery tree. In the algorithm 400, the microvascular resistances are modified only if the current branch is stenosed. If the current branch is stenosed, steps 402-412 are performed for the current branch. If there is no stenosis in the current branch, the algorithm 400 ends for the current branch and can be recursively called for a next branch in the coronary artery tree. For a current branch having a stenosis, at step 402, a resistance $(R_{t-current})_i$ introduced by the stenosis in the current branch is calculated by subtracting a resistance of the stenosis, computed as a ratio of the pressure drop along the stenosis to the flow rate through the stenosis $((P_{in})_i - (P_{out})_i)/Q_i$, from the equivalent microvascular resistance of the current branch $(R_{t-microv})_i$. $(P_{in})_i$ and $(P_{out})_i$ are simulated pressure values at an inlet and outlet of the stenosis, respectively, and $Q_i$ is the simulated blood flow rate through the stenosis.

Figure 5:
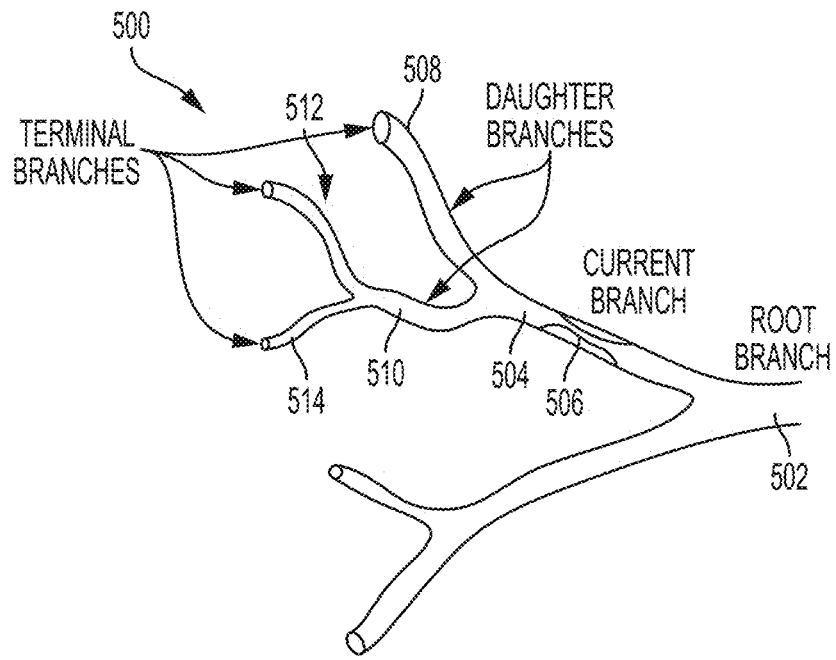
FIG. 5 illustrates an exemplary coronary artery tree with branch labels used in the coronary circulatory autoregulation algorithm.

The algorithm 400 then adapts the resistances of the daughter branches to the current branch as a result of the resistance introduced by the stenosis in the current branch. FIG. 5 illustrates an exemplary coronary artery tree with branch labels used by the coronary autoregulation algorithm of FIG. 4. As shown in FIG. 5, the coronary artery tree 500 shows a root branch 502 and a current branch 504 having a stenosis 506. Branches 508 and 510 are daughter branches to the current branch 504, and branches 508, 512, and 514 are terminal branches. At step 404 of FIG. 4, an equivalent resistance $(R_{t\text{-}downs})_i$ is calculated from the total resistances of the daughter branches j downstream of the current branch i. The resistances of the daughter branches are adapted so as to not to modify the flow rate split ratios of the daughter branches. For each daughter branch j of the current branch i, at step 406, the flow rate split ratio $\Phi_j$ is calculated from the previous value of the downstream resistance for the daughter branch $(R_{t\text{-}microv})_j$ and the equivalent downstream resistance calculated for the current branch $(R_{t\text{-}downs})_i$. At step 408, a new value for the total downstream resistance $(R_{t\text{-}microv})_j$ is calculated for each daughter branch j based on the new resistance value calculated for the current branch $(R_{t\text{-}current})_i$ and the flow rate split ratio calculated for the daughter branch $\Phi_j$.

At step 410, the new values of the downstream resistances are distributed to the terminal branches of each daughter branch, and at step 412, new equivalent microvascular resistances are computed for all of the branches downstream of each daughter branch. For example, steps 410 and 412 can be implemented by repeating calculations similar to those in steps 404, 406, and 408 for downstream branches for each daughter branch until all terminal branches are reached. The autoregulation algorithm 400 can be called for the root branch and then called recursively for each daughter branch, so as to cover the entire coronary tree and modify the terminal resistances while taking into account all stenosed branches in the coronary tree.

As shown in FIG. 3, coronary autoregulation has a limit, i.e. when the mircovascular resistance cannot be decreased below a certain minimum value, which corresponds to the hyperemic state of the patient. Thus, if the stenosis is very severe, coronary autoregulation may reach its limit, and the flow may decrease below the level given by the myocardial demand (myocardial oxygen consumption). Hence, if, as a result of applying algorithm 400 of FIG. 4, a microvascular resistance is decreased below its minimum, hyperemic value, its value is set constant and equal to the hyperemic value.

In an advantageous embodiment, the blood flow and pressure computations can be performed over a plurality of cardiac cycles, with the algorithm for modeling coronary autoregulation performed at the end of each cardiac cycle. Different approaches can be used for matching the blood flow and pressure simulations with non-invasive clinical measurements of the patient in order to achieve patient-specific blood flow and pressure simulations. For example, in a possible implementation, parameters of the computational model of coronary arterial circulation can be directly estimated once prior to simulating the blood flow and pressure. In another possible implementation, iterative estimation can be used to adapt the parameters during the blood flow and pressure computation. It is also possible to use a combination of these approaches. In an advantageous embodiment, after each cardiac cycle, simulated measurements based on the blood flow and pressure computations can be compared to non-invasive measurements of the patient (e.g., systolic and diastolic blood pressure, heart rate, etc.) and one or more parameters of the computational model of coronary arterial circulation or one or more boundary conditions can be refined to minimize a difference between the simulated measurements and the non-invasive measurements acquired for the patient. The blood flow and pressure computations can be performed at least until the simulated measurements converge to the non-invasive measurements of the patient, and iFR and/or other hemodynamic indices can be calculated using the simulated blood flow and pressure values for one or more cardiac cycles after the simulated measurements have converged to the non-invasive measurements of the patient.

Figure 6:
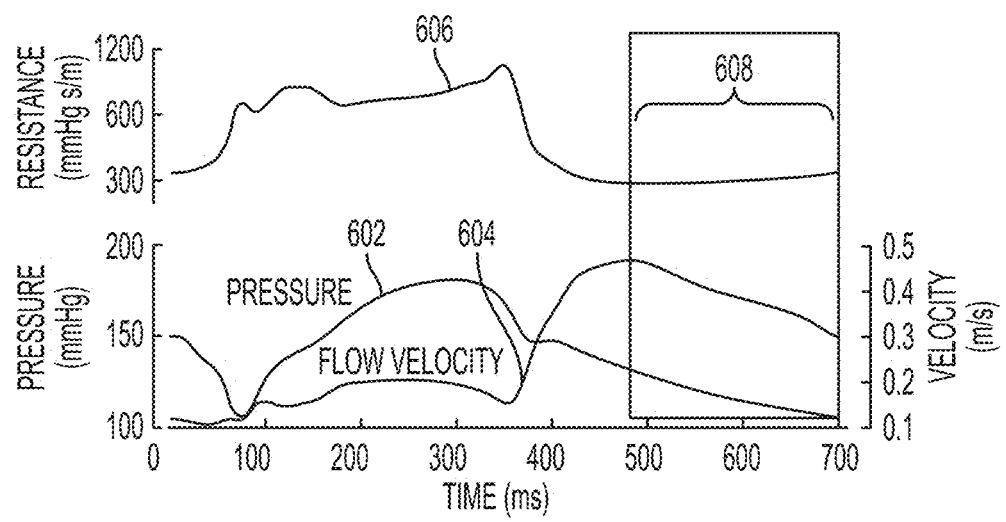
FIG. 6 illustrates a wave-free period on a graph of instantaneous pressure, blood flow velocity, and microvascular resistance during one heart cycle at rest.

Returning to FIG. 1, at step 110, a wave free period is identified in each heart cycle in the blood flow and pressure simulation. As per the definition, iFR is computed from invasively measured pressures obtained during the wave-free period. Instantaneous coronary resistance, calculated as the ratio of instantaneous pressure to instantaneous flow rate, varies during the heart cycle due to the interaction between the microvasculature and the myocardium, with higher fluctuations during systole. During the wave-free period however, coronary resistance is naturally approximately constant and minimized. FIG. 6 illustrates an example of instantaneous pressure values 602, instantaneous flow velocity values 604 and instantaneous coronary resistance values 606 during one cardiac cycle at rest. As shown in FIG. 6, the coronary resistance 606 is naturally constant and minimized during a wave-free period 608.

Figure 7:
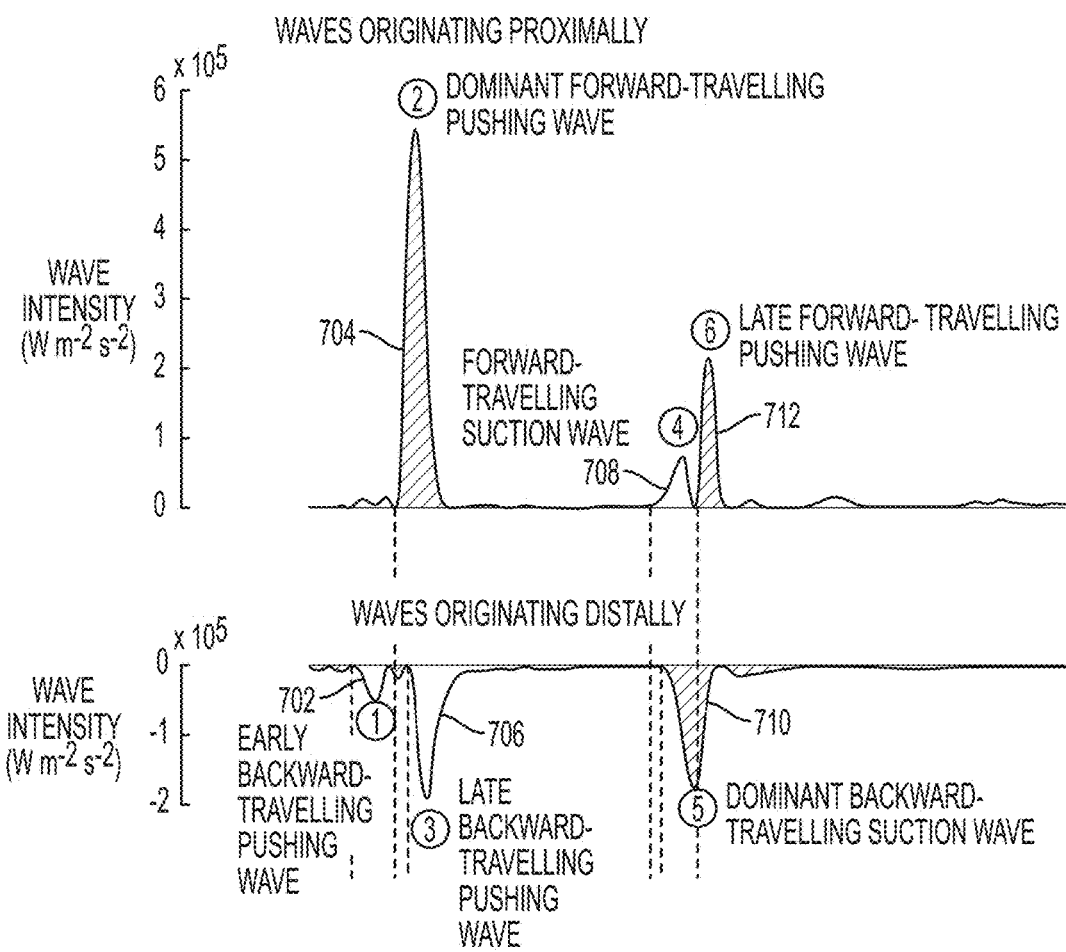
FIG. 7 illustrates identification of waves in a left coronary artery tree.

In order to compute iFR based on the blood flow and pressure simulations, the wave-free period must be determined. In arterial circulation, waves can originate from both upstream locations (e.g. left ventricle), referred to as forward travelling waves, or from downstream locations (e.g., bifurcations or the microcirculation), referred to as backward travelling waves. In order to establish the origin of the waves, both pressure and flow rate profiles are required. In the coronary circulation, forward and backward travelling waves can occur at the same time. To separate the waves, a wave intensity analysis can be performed. FIG. 7 illustrates identification of waves in the human left coronary artery tree. As shown in FIG. 7, six different waves can be identified in the coronary circulation: (1) Early backward-travelling pushing wave 702—at the onset of ventricular contraction, the myocardium compresses the coronary microcirculation; (2) Forward-travelling pushing wave 704—contraction of the ventricle lumen generates ventricular ejection; (3) Late backward-travelling pushing wave 706—appears as a result of continued compression of the micro-circulation and wave reflection of the forward travelling pushing wave; (4) Forward-travelling suction wave 708—the slowing of ventricular contraction creates a suction effect at the proximal ends of the arteries; (5) Dominant backward-travelling suction wave 710—appears as a result of the relief of myocardial compression of the coronary microcirculation; and (6) Late forward-travelling pushing wave 712—is associated with closure of the aortic valve. The diastolic wave-free period runs from $WI_{-[diastole]}=0$ to 5 ms before the end of diastole. The end of diastole is defined as the moment when the early backward-travelling pushing wave 702 is detected. $WI_{-[diastole]}$ is the wave intensity of distally originating waves (backward travelling waves).

In current clinical practice, only time-varying pressure is measured and hence it is not possible to perform wave separation. Consequently, the wave-free period considered for the invasive measurement of iFR typically runs from 25% of the way into diastole (the onset of diastole is identified from the dicrotic notch) to 5 ms before the end of diastole. According to a first possible implementation, the wave-free period in the simulated cardiac cycle can similarly be identified as an interval of time which runs from 25% of the way into diastole to 5 ms before the end of diastole. Other possible implementations that utilize the simulated pressure and/or velocity (flow rate) profiles can also be used to identify the wave-free period. In a second possible implementation, the wave-free period in the simulated cardiac cycle can be identified as an interval of time which begins at 250 ms after $dU_{max}$ is obtained and lasts for 150 ms, where dU is the derivative of the blood velocity with respect to time and $dU_{max}$ is the maximum value of dU within one cardiac cycle. In a third possible implementation, the wave-free period in the simulated cardiac cycle can be identified as an interval of time which runs from 150 ms after a maximum pressure $P_{max}$ is obtained until the end of the cardiac cycle minus 50 ms. In a fourth possible implementation, the wave-free period in the simulated cardiac cycle can be identified as the period, after peak pressure $P_{max}$, during which the standard deviation of the forward travelling wave is in the lowest 5% (or in the lowest 10% if no such period exists for the lowest 5%). In a fifth possible implementation, the wave-free period in the simulated cardiac cycle can be identified as a period that is the mid window between the peak pressure time point and the end of the heart cycle (or a ⅗ window between these two time points). In a sixth possible implementation, the wave-free period in the simulated cardiac cycle can be identified the window during which dU is less than 10% (or 5%) of $dU_{max}$. It is to be understood that the present invention is not limited to these techniques for identifying the wave-free period and any method for identifying the wave-free period may be used in conjunction with the method of FIG. 1

Returning to FIG. 1, at step 112, iFR is calculated for at least one coronary artery stenosis based on the computed pressures in the wave-free period. The iFR for a particular coronary artery stenosis is calculated non-invasively from the computed pressure values in the blood flow and pressure simulation as the ratio of the average computed distal pressure during the wave-free period of the simulated cardiac cycle to the average computed aortic pressure during the wave-free period of the simulated cardiac cycle. In an advantageous implementation, the blood flow and computations are repeated to simulate a plurality of cardiac cycles with the coronary autoregulation algorithm performed at the end of each cardiac cycle. After each simulated cardiac cycle, simulated measurements based on the blood flow and pressure computations are compared to non-invasive measurements of the patient (e.g., systolic and diastolic blood pressure, heart rate, etc.) and one or more parameters of the computational model of coronary arterial circulation or one or more boundary conditions can be refined to minimize a difference between the simulated measurements and the non-invasive measurements acquired for the patient. The computations can be performed until the simulated measurements based on the blood flow and pressure computations converge to the non-invasive measurements of the patient, and the iFR for a particular coronary stenosis can be calculated based on the computed pressure values in the wave-free period of a simulated cardiac cycle for which the simulated measurements have converged to the non-invasive measurements of the patient.

It is also possible that the iFR be calculated for each simulated cardiac cycle or by averaging data from multiple simulated cardiac cycles. A respective iFR value can be non-invasively calculated for each of a plurality of stenoses in the coronary artery tree. Other hemodynamic indices, particularly hemodynamic indices typically measured for a patient at rest, such as rest (basal) $P_d/P_a$, can also be calculated for each coronary artery stenosis from the simulated pressure and/or flow values. It is also to be understood that the iFR (or other hemodynamic indices) can be calculated for any location in the coronary artery tree, and not only at stenoses.

Certain parameters of the microvascular model may further be adapted to ensure that a certain simulated hemodynamic index matches the measured value of that hemodynamic index. For example, since iFR is computed during the wave-free window, it depends on the trans-stenotic pressure drop during diastole (the wave-free period is part of diastole). The pressure drop in turn depends on the flow rate, and hence it is important to control the amount of coronary flow at systole and at diastole. Previous studies that have examined the amount of coronary flow at systole and diastole indicate that systolic flow is proportionally lower in the LCA as compared to the RCA. For example, one could assume, based on literature data, that systolic flow represents 20% of the total coronary flow for LCA branches, and 31% of the total coronary flow for RCA branches. Typical coronary microvascular models use the simulated left/right ventricular pressure in order to model the effect of the cardiac contraction on the flow rate, thus leading to low flow during systole and high flow during diastole (see for example the lumped parameter model 210 in FIG. 2). Furthermore, a proportionality constant c may be used when applying the left/right ventricular pressure in the coronary microvascular models. This proportionality constant may be adapted separately for each outlet branch so as to match a certain ratio of systolic to diastolic flow.

Exemplary results for non-invasively computing iFR from blood flow and pressure simulations based on coronary imaging data obtained from a CT scan are provided for three cases. Case 1 is an anatomically severe stenosis. Case 2 is an anatomically intermediate stenosis. Case 3 is an anatomically mild stenosis. Computations were run until convergence and results are provided herein for only the last heart cycle. Table 1 shows average distal and aortic pressures and pressure ratios (basal $P_d/P_a$ and iFR) for entire cardiac cycle and for the wave-free period for the three cases. In all three cases, both basal $P_d/P_a$ and iFR are computed non-invasively from medical imaging data based on pressure and flow computations using the method of FIG. 1.

TABLE 1

| Configuration | Quantity | Case 1 | Case 2 | Case 3 |
|---|---|---|---|---|
| Entire heart cycle - Rest | $P_a$ [mmHg] | 106.084 | 100.172 | 102.803 |
| | $P_d$ [mmHg] | 59.609 | 95.07 | 100.312 |
| | Basal $P_d/P_a$ | 0.562 | 0.949 | 0.976 |
| Wave-free period - Rest | $P_a$ [mmHg] | 100.051 | 91.895 | 97.233 |
| | $P_d$ [mmHg] | 37.736 | 85.154 | 93.499 |
| | iFR | 0.377 | 0.927 | 0.962 |

Figure 8:
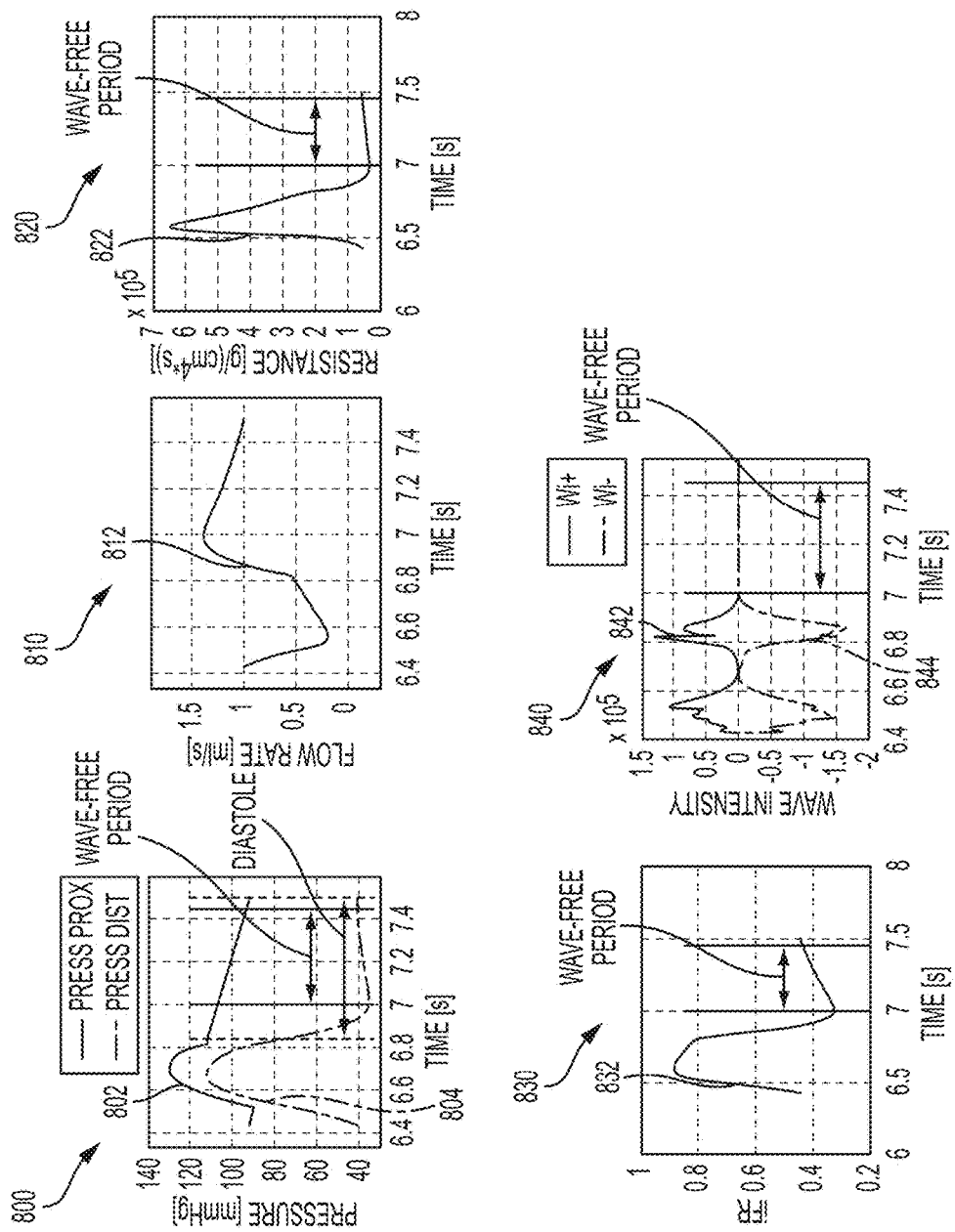
FIG. 8 illustrates exemplary quantities of interest resulting from a blood flow and pressure simulation for an anatomically severe stenosis.

FIG. 8 illustrates exemplary results for simulating blood flow and pressure and calculating iFR for an anatomically severe stenosis (Case 1). As shown in FIG. 8, image 800 shows the computed time-varying proximal (aortic) and distal aortic pressures 802 and 804, respectively, for the stenosis over a cardiac cycle. Image 810 shows the computed time-varying flow rate 812 in the stenosis over the cardiac cycle. Image 820 shows the instantaneous coronary resistance 822 over the cardiac cycle. Image 830 shows the instantaneous distal to proximal pressure ratio 832 over the cardiac cycle. The iFR value is computed by calculating the ratio of the average distal pressure to the average proximal pressure in the wave-free period. Image 840 shows the wave intensity of forward and backward travelling waves 842 and 843, respectively, over the cardiac cycle. The diastolic period runs from 6.828 seconds (dicrotic notch) to 7.5 seconds. The wave-free period, considered for the computation of iFR, runs from 25% of the way into diastole to 5 ms before the end of diastole (6.99 seconds to 7.45 seconds). The resistance 822 is constant during the wave-free period and also the instantaneous distal to proximal pressure ratio 832 is relatively constant during the wave-free period. As shown in image 840, when representing the wave-free window on the plot of the wave intensity of the forward and backward travelling waves 842 and 844, it can be observed that there are no waves in the interval from 6.99 seconds to 7.45 seconds, which was identified as the wave-free period. As shown in Table 1, the computed iFR value for the anatomically severe stenosis in Case 1 is 0.377, which indicates that this stenosis is a hemodynamically significant lesion.

Figure 9:
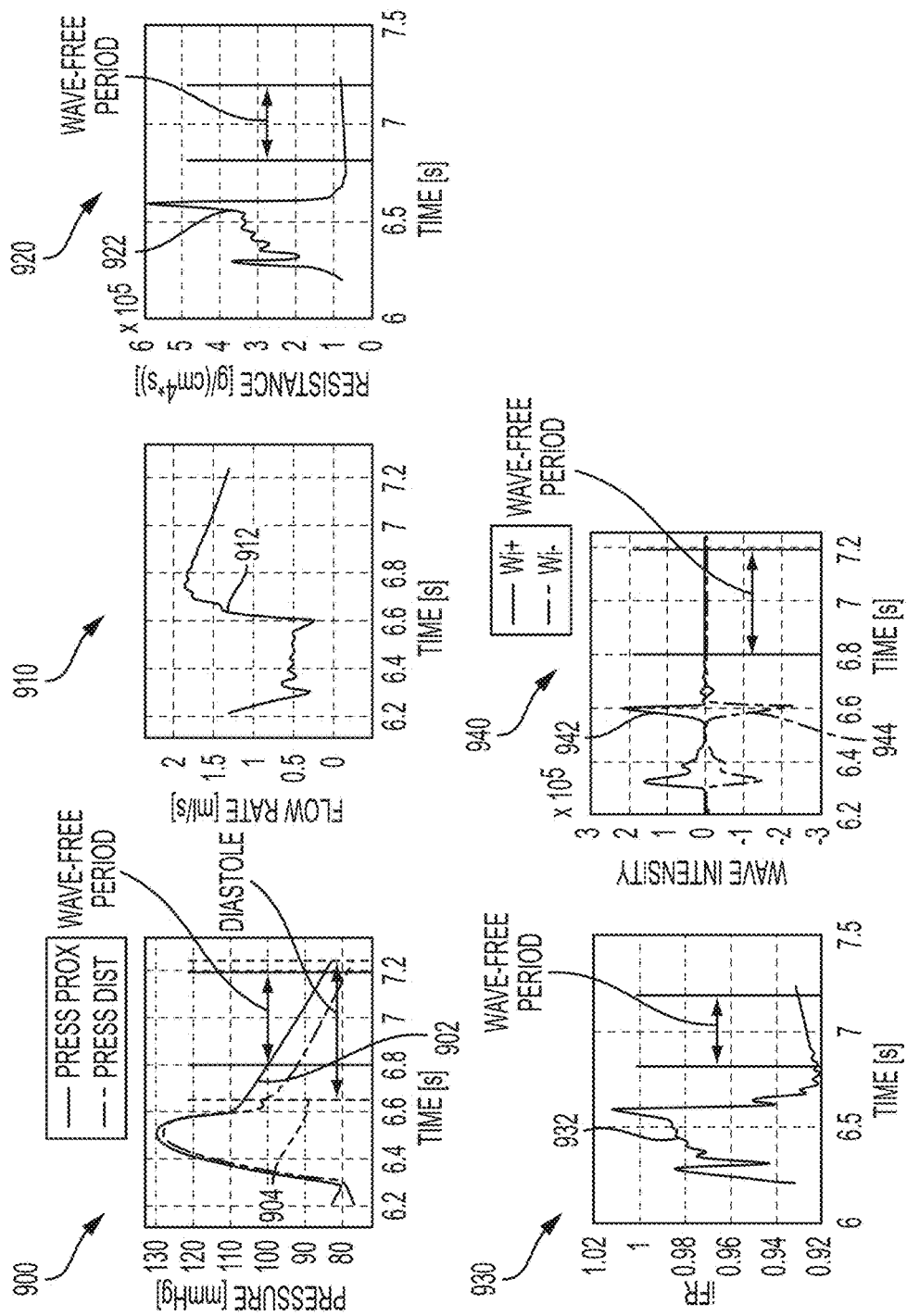
FIG. 9 illustrates exemplary quantities of interest resulting from a blood flow and pressure simulation for an anatomically intermediate stenosis.

FIG. 9 illustrates exemplary results for simulating blood flow and pressure and calculating iFR for an anatomically intermediate stenosis (Case 2). As shown in FIG. 9, image 900 shows the computed time-varying proximal (aortic) and distal aortic pressures 902 and 904, respectively, for the stenosis over a cardiac cycle. Image 910 shows the computed time-varying flow rate 912 in the stenosis over the cardiac cycle. Image 920 shows the instantaneous coronary resistance 922 over the cardiac cycle. Image 930 shows the instantaneous distal to proximal pressure ratio 932 over the cardiac cycle. The iFR value is computed by calculating the ratio of the average distal pressure to the average proximal pressure in the wave-free period. Image 940 shows the wave intensity of forward and backward travelling waves 942 and 943, respectively, over the cardiac cycle. The diastolic period runs from 6.65 seconds to 7.19 seconds. The wave-free period runs from 6.797 seconds to 7.19 seconds. The resistance 922 is constant during the wave-free period and also the instantaneous distal to proximal pressure ratio 932 is relatively constant during the wave-free period. As shown in image 940, it can be observed that there are no waves in the wave-free period. As shown in Table 1, the computed iFR value for the anatomically intermediate stenosis in Case 2 is 0.927, which falls into a grey zone identified in previous studies for which it is not clear if the lesion is hemodynamically significant.

Figure 10:
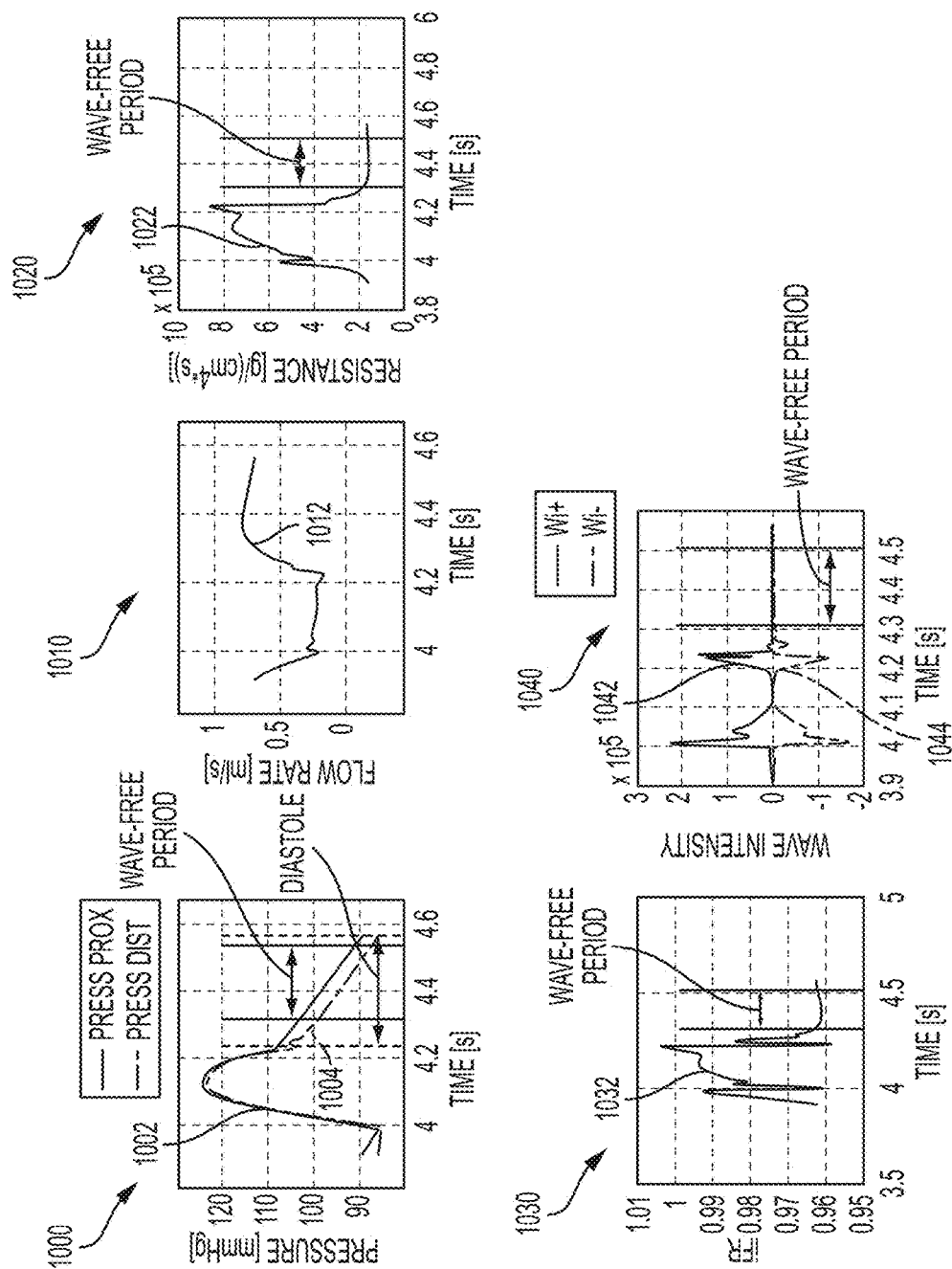
FIG. 10 illustrates exemplary quantities of interest resulting from a blood flow and pressure simulation for an anatomically mild stenosis.

FIG. 10 illustrates exemplary results for simulating blood flow and pressure and calculating iFR for an anatomically mild stenosis (Case 3). As shown in FIG. 10, image 1000 shows the computed time-varying proximal (aortic) and distal aortic pressures 1002 and 1004, respectively, for the stenosis over a cardiac cycle. Image 1010 shows the computed time-varying flow rate 1012 in the stenosis over the cardiac cycle. Image 1020 shows the instantaneous coronary resistance 1022 over the cardiac cycle. Image 1030 shows the instantaneous distal to proximal pressure ratio 1032 over the cardiac cycle. The iFR value is computed by calculating the ratio of the average distal pressure to the average proximal pressure in the wave-free period. Image 1040 shows the wave intensity of forward and backward travelling waves 1042 and 1043, respectively, over the cardiac cycle. The diastolic period runs from 4.235 seconds to 4.565 seconds. The wave-free period runs from 4.317 seconds to 4.515 seconds. The resistance 1022 is constant during the wave-free period and also the instantaneous distal to proximal pressure ratio 1032 is relatively constant during the wave-free period. As shown in image 1040, it can be observed that there are no waves in the wave-free period. As shown in Table 1, the computed iFR value for the anatomically mild stenosis in Case 3 is 0.962, which indicates that this is a hemodynamically non-significant lesion.

Figure 11:
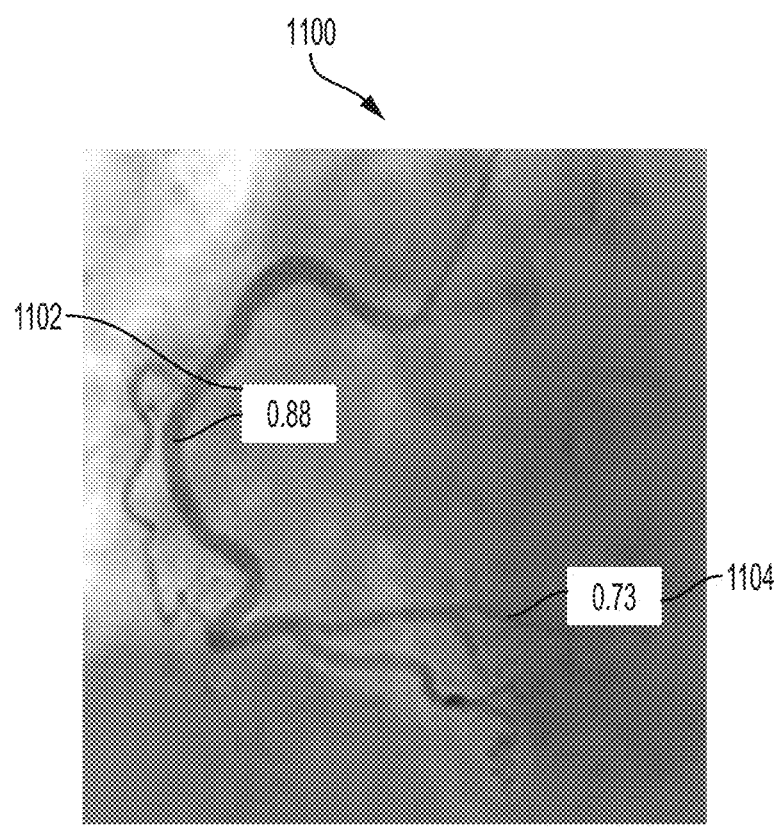
FIG. 11 illustrates an example of visualizing computed iFR values on a medical image.
Figure 12:
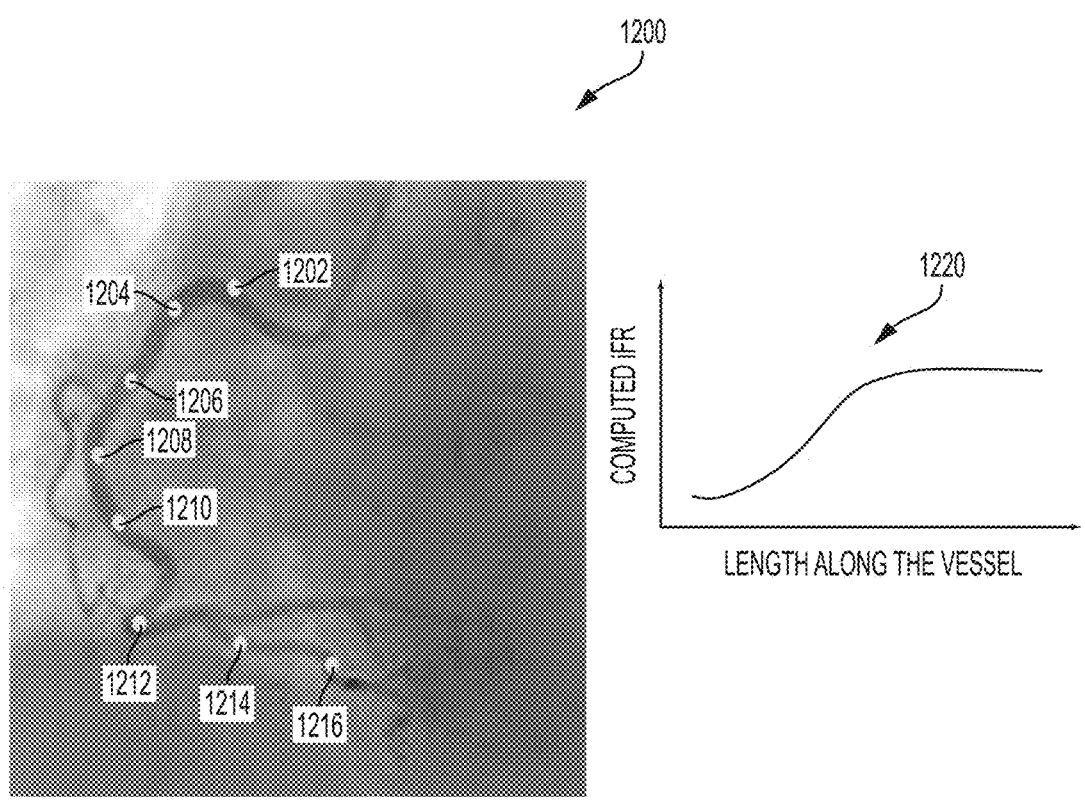
FIG. 12 illustrates an exemplary plot of computed iFR values at selected locations along a vessel.

Once the iFR (or another hemodynamic index) is computed for one or more stenoses using the method of FIG. 1, the computed iFR for each stenosis and the simulation results can be output, for example by being displayed on a display device of a computer system. For example, the simulation results can be output as shown in FIGS. 8, 9, and 10. In a possible implementation, the computed iFR value may be output by simply displaying a listing or table of iFR values for the stenoses. In another possible implementation, one or more computed iFR values can be visualized on a medical image of the patient that is displayed on a display device. FIG. 11 illustrates an example of visualizing iFR values on a medical image. As shown in FIG. 11, a medical image 1100 is displayed and iFR values 1102 and 1104 corresponding to particular locations in the medical image (e.g., stenosis locations) are visualized on the medical image 1100. In another possible implementation a plot of iFR values at selected locations along a vessel can be displayed. FIG. 12 illustrates an exemplary plot of iFR values at selected locations along a vessel. As shown in FIG. 12, image 1200 shows various locations 1202, 1204, 1204, 1206, 1208, 1210, 1212, 1214, and 1216 along a vessel, at which iFR is computed using the method of FIG. 1. Image 1220 shows a plot of computed iFR along the length of the vessel generated based on the computed iFR values at the selected locations 1202, 1204, 1204, 1206, 1208, 1210, 1212, 1214, and 1216 along the vessel.

As described above, the method of FIG. 1 simulates blood flow and pressure in the coronary arteries of a patient and computed iFR and/or other hemodynamic indices from medical image data and non-invasive clinical measurements of the patient. In an alternative embodiment, an aortic pressure measurement for the patient may be determined invasively using a pressure measuring device, such as a pressure wire. In such an embodiment, the aortic pressure measurement may be used in a number of different ways. For example, in a possible implementation, the measured aortic pressure value during the wave-free period may be used in the iFR computation as the denominator in the iFR formula. In another possible implementation, the measured aortic pressure may be used as a boundary condition for the flow and pressure computations. In another possible implementation, the measured aortic pressure may be used to identify the wave-free period. Such embodiments would not require advancing the pressure wire distal to the stenosis, as is done for invasive iFR measurement, thereby reducing the acquisition time and reducing the risk of dislodging the plaque or puncturing the lumen.

Although in the description above, the method is used for computing hemodynamic indices for coronary artery stenoses, the present invention is not limited to coronary arteries and may be similarly applied to other arteries, such as the aorta, renal arteries, cerebral arteries, iliac arteries, supra-aortic arteries, etc. Although the method of claim 1 performs the simulations and identifies the wave-free period at a rest state, the method can be similarly applied for a wave-free window obtained in a maximum vasodilation state or any other intermediate state between rest and maximum vasodilation. When applied at maximum vasalidation, the method can be used to calculate different hemodynamic indices, such as fractional flow reserve (FFR). The method of FIG. 1 can be applied for the entire cardiac cycle, or for any sub-part of the cardiac cycle (e.g., entire systole or a sub-part of systole, diastole or a sub-part of diastole, or combinations thereof). The method of FIG. 1 can be applied not only for the non-invasive computation of pressure-based indices, but also for other indices computed as a combination of coronary pressure, coronary perfusion, and/or coronary resistance.

As described above, the algorithm for modeling coronary circulatory autoregulation can be applied at the end of every cardiac cycle. However, the present invention is not limited thereto, and in various embodiments, the algorithm for modeling coronary circulatory autoregulation can be applied multiple times during a single cardiac cycle (e.g., end of systole and end of diastole) or only after a certain number of cardiac cycles.

Figure 13:
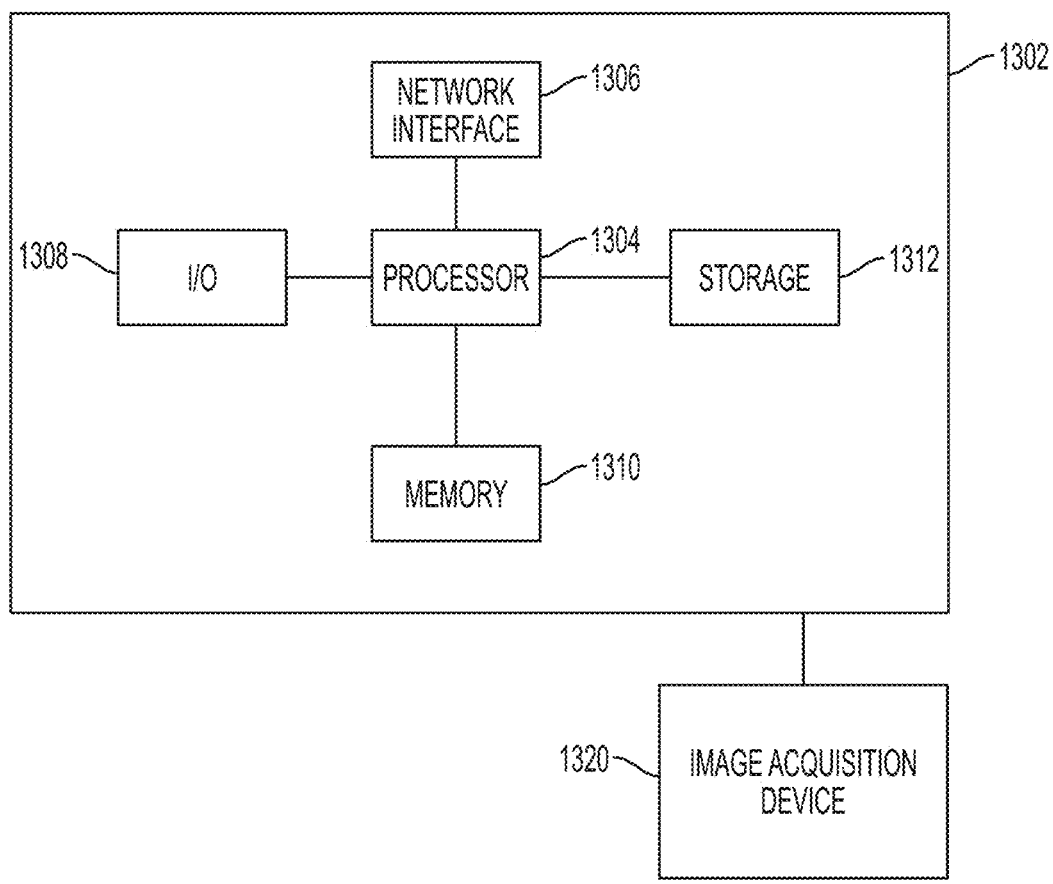
FIG. 13 is a high-level block diagram of a computer capable of implementing the present invention.

The above-described methods for non-invasive computation of hemodynamic indices for coronary artery stenosis may be implemented on a computer using well-known computer processors, memory units, storage devices, computer software, and other components. A high-level block diagram of such a computer is illustrated in FIG. 13. Computer 1302 contains a processor 1304, which controls the overall operation of the computer 1302 by executing computer program instructions which define such operation. The computer program instructions may be stored in a storage device 1312 (e.g., magnetic disk) and loaded into memory 1310 when execution of the computer program instructions is desired. Thus, the steps of the methods of FIGS. 1 and 4 may be defined by the computer program instructions stored in the memory 1310 and/or storage 1312 and controlled by the processor 1304 executing the computer program instructions. An image acquisition device 1320, such as a CT scanning device, MR scanning device, Ultrasound device, etc., can be connected to the computer 1302 to input image data to the computer 1302. It is possible to implement the image acquisition device 1320 and the computer 1302 as one device. It is also possible that the image acquisition device 1320 and the computer 1302 communicate wirelessly through a network. In a possible embodiment, the computer 1302 may be located remotely with respect to the image acquisition device 1320 and the method steps are performed as part of a server or cloud based service. The computer 1302 also includes one or more network interfaces 1306 for communicating with other devices via a network. The computer 1302 also includes other input/output devices 1308 that enable user interaction with the computer 1302 (e.g., display, keyboard, mouse, speakers, buttons, etc.). Such input/output devices 1308 may be used in conjunction with a set of computer programs as an annotation tool to annotate volumes received from the image acquisition device 1320. One skilled in the art will recognize that an implementation of an actual computer could contain other components as well, and that FIG. 13 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for hemodynamic assessment of a coronary artery based on medical image data of a patient, comprising:
   extracting patient-specific anatomical measurements of the coronary arteries from medical image data of a patient;
   calculating patient-specific boundary conditions of a computational model of coronary circulation representing the coronary arteries based on the patient-specific anatomical measurements of the coronary arteries;
   simulating blood flow and pressure in the coronary arteries using the computational model of coronary circulation and the patient-specific boundary conditions and modeling coronary autoregulation during the simulation of blood flow and pressure in the coronary arteries, wherein modeling coronary autoregulation during the simulation of blood flow and pressure in the coronary arteries comprises:
      adapting microvascular resistances at outlets of the computational model of coronary circulation downstream of each coronary artery stenosis in the computational model of coronary circulation based on a simulated pressure drop over the coronary artery stenosis, a simulated flow rate through the coronary artery stenosis, and flow rate split ratios calculated for branches in the coronary artery tree downstream of the coronary artery stenosis; and
   calculating a hemodynamic index for at least one region in the coronary arteries based on the simulated blood flow and pressure.

2. The method of claim 1, wherein adapting microvascular resistances at outlets of the computational model of coronary circulation downstream of each coronary artery stenosis in the computational model of coronary circulation based on a simulated pressure drop over the coronary artery stenosis, a simulated flow rate through the coronary artery stenosis, and flow rate split ratios calculated for branches in the coronary artery tree downstream of the coronary artery stenosis comprises, for each of a plurality of branches in a coronary artery tree of the patient in the computational model of coronary circulation:
   if a current branch includes a stenosis region:
      calculating an adjusted resistance of the current branch by subtracting a resistance of the stenosis region estimated based on simulated pressure and flow values from an equivalent microvascular resistance of the current branch; and
      modifying resistances for all branches in the coronary artery tree downstream of the current branch by distributing the adjusted resistance of the current branch through the branches downstream to terminal branches downstream of the current branch.

3. The method of claim 2, wherein modifying resistances for all branches in the coronary artery tree downstream of the current branch by distributing the adjusted resistance of the current branch through the branches downstream to terminal branches downstream of the current branch comprises:
   calculating an equivalent resistance for the current branch based on equivalent microvascular resistances of daughter branches to the current branch; and
   for each daughter branch to the current branch:
      calculating a flow rate split ratio for the daughter branch based on the equivalent resistance calculated for the current branch and the equivalent microvascular resistance for the daughter branch; and
      calculating an adjusted equivalent microvascular resistance for the daughter branch based on the adjusted resistance of the current branch and the flow rate split ratio calculated for the daughter branch.

4. The method of claim 3, wherein modifying resistances for all branches in the coronary artery tree downstream of the current branch by distributing the adjusted resistance of the current branch through the branches downstream to terminal branches downstream of the current branch further comprises:

for each daughter branch to the current branch:
distributing the adjusted equivalent microvascular resistance for the daughter branch through any branches downstream of the daughter branch to terminal branches downstream of the daughter branch; and
adjusting an equivalent microvascular resistance of each branch downstream of the daughter branch based on the adjusted equivalent microvascular resistance of the daughter branch.

5. The method of claim 3, wherein calculating an adjusted resistance of the current branch by subtracting a resistance of the stenosis region estimated based on simulated pressure and flow values from an equivalent microvascular resistance of the current branch comprises:

calculating the adjusted resistance $(R_{t\text{-}current})_i$ of the current branch i as $(R_{t\text{-}current})_i = (R_{t\text{-}microv})_i - ((P_{in})_i - (P_{out})_i)/Q_i$, where $(R_{t\text{-}microv})_i$ is the equivalent microvascular resistance of the current branch, $((P_{in})_i - (P_{out})_i)/Q_i$ is the resistance of the stenosis region in the current branch, $(P_{in})_i - (P_{out})_i$ is a simulated pressure drop over the stenosis region in the current branch, and $Q_i$ is a simulated flow rate through the stenosis region in the current branch.

6. The method of claim 5, wherein calculating an equivalent resistance for the current branch based on equivalent microvascular resistances of daughter branches to the current branch comprises:

calculating the equivalent resistance $(R_{t\text{-}downs})_i$ for the current branch i as $(R_{t\text{-}downs})_i = 1/\Sigma_j 1/(R_{t\text{-}microv})_j$, where $(R_{t\text{-}microv})_j$ is the equivalent microvascular resistance of a daughter branch j to the current branch.

7. The method of claim 6, wherein calculating a flow rate split ratio for the daughter branch based on the equivalent resistance calculated for the current branch and the equivalent microvascular resistance for the daughter branch comprises:

calculating the flow rate split ratio $\Phi_j$ for the daughter branch j as $\Phi_j = (R_{t\text{-}downs})_i/(R_{t\text{-}microv})_j$.

8. The method of claim 7, wherein calculating an adjusted equivalent microvascular resistance for the daughter branch based on the adjusted resistance of the current branch and the flow rate split ratio calculated for the daughter branch comprises:

calculating the adjusted equivalent microvascular resistance for the daughter branch j as $(R_{t\text{-}microv})_j = (R_{t\text{-}current})_i/\Phi_j$.

9. The method of claim 1, wherein modeling coronary autoregulation during the simulation of blood flow and pressure in the coronary arteries further comprises:

modeling coronary autoregulation at an end of each of a plurality of simulated cardiac cycles during the simulation of blood flow and pressure in the coronary arteries.

10. The method of claim 1, further comprising:
identifying a wave-free period in at least one simulated cardiac cycle in the simulation of blood flow and pressure in the coronary arteries.

11. The method of claim 10, wherein identifying a wave-free period in at least one simulated cardiac cycle in the simulation of blood flow and pressure in the coronary arteries comprises:

identifying the wave-free period as an interval of time that runs from 25% of the way into diastole to 5 ms before the end of diastole in the at least one simulated cardiac cycle.

12. The method of claim 10, wherein identifying a wave-free period in at least one simulated cardiac cycle in the simulation of blood flow and pressure in the coronary arteries comprises:

identifying the wave-free period as an interval of time that begins 250 ms after a maximum value of a derivative of simulated blood flow velocity in the at least one simulated cardiac cycle and lasts for 150 ms.

13. The method of claim 10, wherein identifying a wave-free period in at least one simulated cardiac cycle in the simulation of blood flow and pressure in the coronary arteries comprises:

identifying the wave-free period as an interval of time that runs from 150 ms after a maximum simulated pressure in the at least one simulated cardiac cycle until an end of the at least one simulated cardiac cycle minus 50 ms.

14. The method of claim 10, wherein identifying a wave-free period in at least one simulated cardiac cycle in the simulation of blood flow and pressure in the coronary arteries comprises:

identifying the wave-free period as a period after a maximum simulated pressure in the at least one simulated cardiac cycle during which a standard deviation of a forward travelling wave is in a lowest predetermined percentage.

15. The method of claim 10, wherein identifying a wave-free period in at least one simulated cardiac cycle in the simulation of blood flow and pressure in the coronary arteries comprises:

identifying the wave-free period as a period that is a mid-window between a simulated peak pressure time point in the at least one simulated cardiac cycle and an end of the at least one simulated cardiac cycle.

16. The method of claim 10, wherein identifying a wave-free period in at least one simulated cardiac cycle in the simulation of blood flow and pressure in the coronary arteries comprises:

identifying the wave-free period as a period during the at least one simulated cardiac cycle during which a derivative of simulated blood flow velocity is less than a predetermined percentage of a maximum value of the derivative of the simulated blood flow velocity in the at least one simulated cardiac cycle.

17. The method of claim 10, wherein calculating a hemodynamic index for at least one region in the coronary arteries based on the simulated blood flow and pressure comprises:

calculating an instantaneous wave-Free Ratio (iFR) value for at least one stenosis region based on simulated pressure values in the wave-free period identified in the at least one simulated cardiac cycle.

18. The method of claim 17, wherein calculating an instantaneous wave-Free Ratio (iFR) value for the at least one stenosis region based on simulated pressure values in the wave-free period identified in the at least one simulated cardiac cycle comprises:

calculating a ratio of an average simulated pressure distal to the at least one stenosis region in the wave-free period identified in the at least one simulated cardiac cycle to an average simulated aortic pressure in the wave-free period identified in the at least one simulated cardiac cycle.

19. The method of claim 17, wherein the medical image of the patient is acquired at a rest state of the patient and simulating blood flow and pressure in the coronary arteries using the computational model of coronary circulation and the patient-specific boundary conditions and modeling coronary autoregulation during the simulation of blood flow and pressure in the coronary arteries comprises:
   simulating rest-state blood flow and pressure in coronary arties and modeling coronary autoregulation during the simulation of the rest-state blood flow and pressure in the coronary arteries.

20. The method of claim 1, further comprising:
   displaying a medical image of the patient with a visualization of the calculated hemodynamic index for the at least one region in the coronary arteries displayed on the medical image.

21. The method of claim 1, further comprising:
   calculating the hemodynamic index at a plurality of locations along a coronary artery; and
   displaying a plot of the hemodynamic index over a length of the coronary artery based on the calculated hemodynamic index at the plurality of locations.

22. The method of claim 1, wherein simulating blood flow and pressure in the coronary arteries using the computational model of coronary circulation and the patient-specific boundary conditions and modeling coronary autoregulation during the simulation of blood flow and pressure in the coronary arteries comprises:
   adjusting at least one parameter of the computational model of coronary circulation to minimize a difference between simulated measurements resulting from the simulation of blood flow and pressure and non-invasive clinical measurements of the patient.

23. The method of claim 1, wherein simulating blood flow and pressure in the coronary arteries using the computational model of coronary circulation and the patient-specific boundary conditions and modeling coronary autoregulation during the simulation of blood flow and pressure in the coronary arteries comprises:
   adjusting at least one parameter of the computational model of coronary circulation such that the hemodynamic index calculated based on the simulated blood flow and pressure matches a measured value of the hemodynamic index.

24. The method of claim 23, wherein adjusting at least one parameter of the computational model of coronary circulation such that the hemodynamic index calculated based on the simulated blood flow and pressure matches a measured value of the hemodynamic index comprises:
   adjusting a proportionality constant for each of a plurality of outlet branches of the computational model of coronary circulation to match a target ratio of systolic to diastolic flow.

25. An apparatus for hemodynamic assessment of a coronary artery based on medical image data of a patient, comprising:
   means for extracting patient-specific anatomical measurements of the coronary arteries from medical image data of a patient;
   means for calculating patient-specific boundary conditions of a computational model of coronary circulation representing the coronary arteries based on the patient-specific anatomical measurements of the coronary arteries;
   means for simulating blood flow and pressure in the coronary arteries using the computational model of coronary circulation and the patient-specific boundary conditions;
   means for modeling coronary autoregulation during the simulation of blood flow and pressure in the coronary arteries, wherein the means for modeling coronary autoregulation during the simulation of blood flow and pressure in the coronary arteries comprises:
      means for adapting microvascular resistances at outlets of the computational model of coronary circulation downstream of a coronary artery stenosis based on a simulated pressure drop over the coronary artery stenosis, a simulated flow rate through the coronary artery stenosis, and flow rate split ratios calculated for branches in the coronary artery tree downstream of the coronary artery stenosis; and
   means for calculating a hemodynamic index for at least one region in the coronary arteries based on the simulated blood flow and pressure.

26. The apparatus of claim 25, wherein the means for modeling coronary autoregulation during the simulation of blood flow and pressure in the coronary arteries further comprises:
   means for modeling coronary autoregulation at an end of each of a plurality of simulated cardiac cycles during the simulation of blood flow and pressure in the coronary arteries.

27. The apparatus of claim 25, further comprising:
   means for identifying a wave-free period in at least one simulated cardiac cycle in the simulation of blood flow and pressure in the coronary arteries.

28. The apparatus of claim 27, wherein the means for calculating a hemodynamic index for at least one region in the coronary arteries based on the simulated blood flow and pressure comprises:
   means for calculating an instantaneous wave-Free Ratio (iFR) value for at least one stenosis region based on simulated pressure values in the wave-free period identified in the at least one simulated cardiac cycle.

29. A non-transitory computer readable medium storing computer program instructions for hemodynamic assessment of a coronary artery based on medical image data of a patient, the computer program instructions when executed by a processor cause the processor to perform operations comprising:
   extracting patient-specific anatomical measurements of the coronary arteries from medical image data of a patient;
   calculating patient-specific boundary conditions of a computational model of coronary circulation representing the coronary arteries based on the patient-specific anatomical measurements of the coronary arteries;
   simulating blood flow and pressure in the coronary arteries a using the computational model of coronary circulation and the patient-specific boundary conditions and modeling coronary autoregulation during the simulation of blood flow and pressure in the coronary arteries, wherein modeling coronary autoregulation during the simulation of blood flow and pressure in the coronary arteries comprises:
      adapting microvascular resistances at outlets of the computational model of coronary circulation downstream of each coronary artery stenosis in the computational model of coronary circulation based on a simulated pressure drop over the coronary artery stenosis, a simulated flow rate through the coronary artery stenosis, and flow rate split ratios calculated for branches in the coronary artery tree downstream of the coronary artery stenosis; and calculating a hemodynamic index for at least one region in the coronary arteries based on the simulated blood flow and pressure.

30. The non-transitory computer readable medium of claim 29, wherein adapting microvascular resistances at outlets of the computational model of coronary circulation downstream of each coronary artery stenosis in the computational model of coronary circulation based on a simulated pressure drop over the coronary artery stenosis, a simulated flow rate through the coronary artery stenosis, and flow rate split ratios calculated for branches in the coronary artery tree downstream of the coronary artery stenosis comprises, for each of a plurality of branches in a coronary artery tree of the patient in the computational model of coronary circulation:

if a current branch includes a stenosis region:
calculating an adjusted resistance of the current branch by subtracting a resistance of the stenosis region estimated based on simulated pressure and flow values from an equivalent microvascular resistance of the current branch; and modifying resistances for all branches in the coronary artery tree downstream of the current branch by distributing the adjusted resistance of the current branch through the branches downstream to terminal branches downstream of the current branch.

31. The non-transitory computer readable medium of claim 30, wherein modifying resistances for all branches in the coronary artery tree downstream of the current branch by distributing the adjusted resistance of the current branch through the branches downstream to terminal branches downstream of the current branch comprises:

calculating an equivalent resistance for the current branch based on equivalent microvascular resistances of daughter branches to the current branch; and for each daughter branch to the current branch:
calculating a flow rate split ratio for the daughter branch based on the equivalent resistance calculated for the current branch and the equivalent microvascular resistance for the daughter branch; and calculating an adjusted equivalent microvascular resistance for the daughter branch based on the adjusted resistance of the current branch and the flow rate split ratio calculated for the daughter branch.

32. The non-transitory computer readable medium of claim 31, wherein modifying resistances for all branches in the coronary artery tree downstream of the current branch by distributing the adjusted resistance of the current branch through the branches downstream to terminal branches downstream of the current branch further comprises:

for each daughter branch to the current branch:
distributing the adjusted equivalent microvascular for the daughter branch through any branches downstream of the daughter branch to terminal branches downstream of the daughter branch; and adjusting an equivalent microvascular resistance of each branch downstream of the daughter branch based on the adjusted equivalent microvascular resistance of the daughter branch.

33. The non-transitory computer readable medium of claim 29, wherein modeling coronary autoregulation during the simulation of blood flow and pressure in the coronary arteries further comprises:

modeling coronary autoregulation at an end of each of a plurality of simulated cardiac cycles during the simulation of blood flow and pressure in the coronary arteries.

34. The non-transitory computer readable medium of claim 29, further comprising:

identifying a wave-free period in at least one simulated cardiac cycle in the simulation of blood flow and pressure in the coronary arteries.

35. The non-transitory computer readable medium of claim 34, wherein calculating a hemodynamic index for at least one region in the coronary arteries based on the simulated blood flow and pressure comprises:

calculating an instantaneous wave-Free Ratio (iFR) value for at least one stenosis region based on simulated pressure values in the wave-free period identified in the at least one simulated cardiac cycle.

36. The non-transitory computer readable medium of claim 35, wherein calculating an instantaneous wave-Free Ratio (iFR) value for the at least one stenosis region based on simulated pressure values in the wave-free period identified in the at least one simulated cardiac cycle comprises:

calculating a ratio of an average simulated pressure distal to the at least one stenosis region in the wave-free period identified in the at least one simulated cardiac cycle to an average simulated aortic pressure in the wave-free period identified in the at least one simulated cardiac cycle.

37. The non-transitory computer readable medium of claim 35, wherein the medical image of the patient is acquired at a rest state of the patient and simulating blood flow and pressure in the coronary arteries using the computational model of coronary circulation and the patient-specific boundary conditions and modeling coronary autoregulation during the simulation of blood flow and pressure in the coronary arteries comprises:

simulating rest-state blood flow and pressure in coronary arties and modeling coronary autoregulation during the simulation of the rest-state blood flow and pressure in the coronary arteries.

* * * * *